US012421531B2

(12) # United States Patent
Hong et al.

(10) Patent No.: US 12,421,531 B2
(45) Date of Patent: Sep. 23, 2025

(54) TRANSAMINASE MUTANT AND USE THEREOF

(71) Applicant: ASYMCHEM LABORATORIES (FUXIN) CO., LTD., Liaoning (CN)

(72) Inventors: Hao Hong, Morrisville, NC (US); Gage James, Morrisville, NC (US); Yi Xiao, Tianjin (CN); Fang Liu, Tianjin (CN); Na Zhang, Tianjin (CN); Zujian Wang, Tianjin (CN); Junjie Yan, Tianjin (CN); Wanming Shi, Tianjin (CN); Mujiao Zhang, Tianjin (CN); Ye Liu, Tianjin (CN)

(73) Assignee: ASYMCHEM LABORATORIES (FUXIN) CO., LTD., Liaoning (CN)

( * ) Notice: Subject to any disclaimer, the term of this patent is extended or adjusted under 35 U.S.C. 154(b) by 615 days.

(21) Appl. No.: 17/755,266

(22) PCT Filed: Oct. 25, 2019

(86) PCT No.: PCT/CN2019/113430
§ 371 (c)(1),
(2) Date: Apr. 25, 2022

(87) PCT Pub. No.: WO2021/077425
PCT Pub. Date: Apr. 29, 2021

(65) Prior Publication Data

US 2022/0380817 A1 Dec. 1, 2022

(51) Int. Cl.

| | |
|---|---|
| ***C12P 13/00*** | (2006.01) |
| ***C12N 1/20*** | (2006.01) |
| ***C12N 1/21*** | (2006.01) |
| ***C12N 9/10*** | (2006.01) |
| ***C12N 15/70*** | (2006.01) |
| ***C12R 1/19*** | (2006.01) |

(52) U.S. Cl.
CPC ............ *C12P 13/001* (2013.01); *C12N 1/205* (2021.05); *C12N 9/1096* (2013.01); *C12N 15/70* (2013.01); *C12Y 206/01* (2013.01); *C12N 2800/101* (2013.01); *C12R 2001/19* (2021.05)

(58) Field of Classification Search
None
See application file for complete search history.

(56) References Cited

U.S. PATENT DOCUMENTS

2002/0127664 A1 9/2002 Takashima et al.

FOREIGN PATENT DOCUMENTS

| | | | | | |
|---|---|---|---|---|---|
| CN | 105018440 | A | | 11/2015 | |
| CN | 105441404 | A | | 3/2016 | |
| CN | 106801043 | A | | 6/2017 | |
| CN | 107828751 | A | | 3/2018 | |
| CN | 108823179 | A | * | 11/2018 | ........... C12N 9/1096 |
| CN | 108866021 | A | | 11/2018 | |
| CN | 109234327 | A | | 1/2019 | |
| EP | 3486324 | A1 | * | 5/2019 | ........... C07C 211/63 |
| WO | 2010099501 | A2 | | 9/2010 | |
| WO | 2015078258 | A1 | | 6/2015 | |
| WO | 2019084950 | A1 | | 5/2019 | |
| WO | 2019096973 | A1 | | 5/2019 | |

OTHER PUBLICATIONS

Rosetta™ (DE3) Competent Cells, Safety Data Sheet, Sigma-Aldrich, 2025. (Year: 2025).*

"Aminotransferase IV [*Sciscionella* sp. SE31]", XP055803617, retrieved from NCBI Database accession No. WP_031466213, Database Protein, Aug. 3, 2014, 1-13, See Features and Origin.

* cited by examiner

*Primary Examiner* — Todd M Epstein
(74) *Attorney, Agent, or Firm* — NKL Law; Allen Xue

(57) ABSTRACT

An amino acid sequence of the transaminase mutant is an amino acid sequence obtained by a mutation of an amino acid sequence is shown in SEQ ID NO: 1. The mutation occurred at least one of the following mutation sites: G17V, L36P, Q40H, G69Y, H70T, L73A, V77G, V77S, V77T, A78I, Y130M, Y130V, Y130T, N132I, N132T, K141S, K142S, K142T, R143P, G144F, G144W, G144Y, E145D, E145S, E145G, K146R, L148A, L148I and the like.

20 Claims, No Drawings

Specification includes a Sequence Listing.

TRANSAMINASE MUTANT AND USE THEREOF

INCORPORATION OF SEQUENCE LISTING

This application contains a sequence listing submitted in Computer Readable Form (CRF). The CFR file containing the sequence listing entitled "PAL2345412_ST25.txt", which was created on Apr. 25, 2022, and is 3,211 bytes in size. The information in the sequence listing is incorporated herein by reference in its entirety.

TECHNICAL FIELD

The present disclosure relates to the field of biotechnologies, in particular to a transaminase mutant and use thereof.

BACKGROUND

Optically pure amines and a- and b-amino acids play a key role in living organisms. These compounds are also very important in medical applications and are important intermediates for the synthesis of chiral drugs and natural products and the like. There are significant differences in the pharmacological activity, metabolic process and toxicity of enantiomers of chemical drugs containing chiral factors in a human body. The existing research on the chiral drugs becomes one of the main directions of the international new drug research already.

Chiral amines are an important constituent part of the synthesis of a variety of bioactive compounds and active pharmaceutical ingredients. It is estimated that 40% of existing drugs are the chiral amines and derivatives thereof, such as the synthesis of neurological drugs, cardiovascular drugs, antihypertensive drugs, anti-infective drugs and vaccines and the like all use the chiral amines as intermediates (Top. Catal. 2014,57,284-300), so that chiral amine compounds become an important constituent part of the pharmaceutical industry.

There are many types of the industrial production of the chiral amines, it mainly relies on the metal-catalyzed hydrogenation of an enamide from a ketone precursor. The process requires expensive transition metal complexes as a catalyst. Due to limited resources of these transition metal complexes, it is difficult to achieve the sustainability. At the same time, the process of the asymmetric synthesis of the chiral amines from the ketone precursor requires steps of amine protection and deprotection, the steps and wastes are increased, and a yield is reduced. In a method of synthesizing the chiral amine by a catalytic hydrogenation reduction method, the preparation of the catalyst is difficult and expensive, the device investment is large, the production cost is high, the requirements to catalyst activity and hydrogenation conditions are very high, and the catalyst is toxic, especially a sulfide in hydrogen, it is highly prone to personal poisoning.

A transaminase is a type of biological catalysts with proteins as a main body. The transaminase is a general term for enzymes that use a pyridoxal phosphate as a cofactor, and may catalyze the transfer of an amino group on one amino donor (amino acid or amine) to a prochiral acceptor ketone, as to obtain a chiral amine or a by-product ketone or an α-keto acid. Because a traditional chemical method for the asymmetric synthesis of the amine has different limitations, such as low efficiency, low selectivity and more serious environmental pollution. At the same time, the synthesis of the chiral amine catalyzed by the transaminase has high stereo and chemoselectivity, has the safety and environmental compatibility, and is a green and environment-friendly process with one-step catalysis in place, and with incomparable advantages over the chemical method. The synthesis of the chiral compound by the transaminase becomes a key asymmetric synthesis technology.

A substrate spectrum of a natural transaminase is often narrow and may only catalyze a specific type of a substrate to generate the chiral amine. In the synthesis of bioactive compounds or active drugs, many types of the chiral amines are required as a raw material for the synthesis. Therefore, a wide application of the transaminase is limited. At the same time, an industrial production process often requires a certain organic solvent, a pressure, a pH and other conditions that are easy to denature the proteins. Therefore, a biocatalyst used needs to have the higher stability to meet the needs of the industrial production. However, a wild transaminase is often inactivated more easily under stringent conditions and has the poorer stability, thereby the wide application thereof is limited.

Although the progress of using the transaminase to produce the chiral amine is highly concerned already, there are many problems in applications of an enzymatic method for preparing the chiral amine compounds. For example, there is no catalytic activity for a substrate with a large steric hindrance; the fermentation cost is increased because of the low enzyme activity and large amount of the enzyme used; and the stability of a reaction system is not high and it is easy to inactivate and the like. Therefore, it is necessary to modify the natural transaminase to expand the substrate spectrum thereof, so that it acquires the ability to catalyze a substrate with a larger steric hindrance, and at the same time, the stability thereof is improved, as to improve an application value thereof.

SUMMARY

The present disclosure aims to provide a transaminase mutant and use thereof, as to solve a technical problem in an existing technology that an SsTA protein has no catalytic activity on a carbonyl substrate with a larger steric hindrance.

In order to achieve the above purpose, according to one aspect of the present disclosure, a transaminase mutant is provided. An amino acid sequence of the transaminase mutant is an amino acid sequence obtained by a mutation of an amino acid sequence shown in SEQ ID NO:1, and the mutation at least includes one of the following mutation sites: G17V, L36P, Q40H, G69Y, H70T, L73A, V77G, V77S, V77T, A78I, Y130M, Y130V, Y130T, N132I, N132T, K141S, K142S, K142T, R143P, G144F, G144W, G144Y, E145D, E145S, E145G, K146R, L148A, L148I, L148T, L151A, L151H, L151E, L151V, L151Q, T152R, H153P, H153G, Y158S, I160C, L163Q, L163R, A165I, P167S, E170R, T175A, P180A, Y198F, S207I, T290S, T290G, A292G, Y198M, R216Q, R216E, R216S, S217N, W200A, F208R, F208L and F208V; or the amino acid sequence of the transaminase mutant has the mutation site in the mutated amino acid sequence, and has more than 80% identity with the mutated amino acid sequence.

Further, the amino acid sequence of the transaminase mutant is the amino acid sequence obtained by the mutation of the amino acid sequence shown in SEQ ID NO:1, and the mutation also at least includes one of the following mutation sites: T66M, T66A, T66Q, T66S, E105D, T134A. K150N, G187S, R188L, Y158N, I160F, 1160L, I160V. Y162F, T204N, T204S, K211H, K211Q, L237Q, A242T, V244M, V244S, V244D, V244N, V244H, V244E, V244A, Y260F, Y260N, E261 D, T270A, R273S, R273C, R273T, S278R, D327M and E282K; or the amino acid sequence of the transaminase mutant has the mutation site in the mutated amino acid sequence, and has more than 80% identity with the mutated amino acid sequence.

Further, the mutation at least includes one of the following mutation site combinations: L73A+V77G+T290S, H70T+L73A+V77G+A78I+K141S+R143P+S207I+T290S+A292G or H70T+L73A+V77G+G144F/Y/W+S207I.

Further, the mutation at least includes one of the following mutation site combinations: G69Y+H70T+L73A+V77G+A78I+K141S+K142S+R143P+G144F+S207I+T290S+A292G, G69Y+H70T+L73A+V77G+A78I+K141S+K142S+R143P+G144F+S207I+T290S+A292G+A165I, G69Y+H70T+L73A+V77G+A78I+K141S+K142S+R143P+G144W+S207I+T290S+A292G+A165I+Y198M, G69Y+H70T+L73A+V77G+A78I+K141S+K142S+R143P+G144F+S207I+T290S+A292G+A 165I+Y198M, G69Y+H70T+L73A+V77G+A78I+K141S+K142S+R143P+G144F+S207I+T290S+A292G+A165I+R216Q, G69Y+H70T+L73A+V77G+A78I+K141S+K142S+R143P+G144F+S207I+T290S+A292G+A165I+R216S, G69Y+H70T+L73A+V77G+A78I+K141S+K142S+R143P+G144F+S207I+T290S+A292G+A165I+Y198F, G69Y+H70T+L73A+V77G+A78I+K141S+K142S+R143P+G144F+S207I+T290S+A292G+A165I+F208R, G69Y+H70T+L73A+V77G+A78I+K141S+K142S+R143P+G144F+S207I+T290S+A292G+A165I+T204N, G69Y+H70T+L73A+V77G+A78I+K141S+K142S+R143P+G144F+S207I+T290S+A292G+A165I+K211H, G69Y+H70T+L73A+V77G+A78I+K141S+K142S+R143P+G144F+S207I+T290S+A292G+A165I+F144W+Y198F, G69Y+H70T+L73A+V77G+A78I+K141S+K142S+R143P+G144W+S207I+T290S+A292G+A165I+Y198F+K211H, G69Y+H70T+L73A+V77G+A78I+K141S+K142S+R143P+G144F+S207I+A165I+Y130M+163Q+T290S+A292G, G69Y+H70T+L73A+V77G+A78I+K141S+K142S+R143P+G144F+A165I+Y130M+L163Q+Y198F+S207I+T290S+A292G, G69Y+H70T+L73A+V77G+A78I+K141S+K142S+R143P+G144F+A165+Y130M+L163Q+Y158S+I160C+N132T+S207I+T290S+A292G, G69Y+H70T+L73A+V77G+A78I+K141S+K142S+R143P+G144F+A165I+Y130M+L1630+K211H+F208R+S207I+T290S+A292G, G69Y+H70T+L73A+V77G+A78I+K141S+K142S+R143P+G144F+A165I+Y130M+L163Q+Y158S+1160C+S207I+T290S+A292G, G69Y+H70T+L73A+V77G+A78I+K141S+K142T+R143P+G144F+A165I+Y130M+L163Q+K211H+F208R+S207I+T290S+A292G, G69Y+H70T+L73A+V77G+A78I+K141S+K142S+R143P+G144F+L148A+A165I+Y130M+L163Q+K211H+F208R+S207I+T290S+A292G, G69Y+H70T+L73A+V77G+A78I+K141S+K142S+R143P+G144F+L148I+A165I+Y130M+L163Q+K211H+F208R+S207I+T290S+A292G, G69Y+H70T+L73A+V77G+A78I+K141S+K142S+R143P+G144F+A165I+Y130M+L163Q+L151A+S207I+F208R+K211H+T290S+A292G, G69Y+H70T+L73A+V77G+A78I+K141S+K142S+R143P+G144F+P180A+A16511+Y30M+L163Q+F208R+S207I+K211H+T290S+A292G, G69Y+H70T+L73A+V77G+A78I+K141S+K142T+R143P+G144F+L148A+L151A+A165I+Y 130M+L163Q+K211H+F208R+S207I+T290S+A292G, G69Y+H70T+L73A+V77G+A78I+K141S+K142T+R143P+G144F+L148A+L151A+A165I+Y 130M+L163R+K211H+F208R+S207I+T290S+A292G, MTTTEFANREFH+G69Y+H70T+L73A+V77G+A78I+K141S+K142T+R143P+G144Y+L148A+L151A+A165I+Y130M+L163Q+K211H+F208R+S207I+T290S+A292G, G69Y+H70T+L73A+V77G+A78I+Y130V+K141S+K142T+R143P+G144F+E145D+L148T+L151A+A165I+LL163Q+F208R+S207I+K211H+T290S+A292G. MTTTE-FANREFH+G69Y+H70T+L73A+V77G+A78I+K141S+K142T+R1143P+G144Y+L148A+L151A+Y130T+L163Q+A165I+K211H+F208R+S207I+T290S+A292G, MTTTEFANREFH+G69Y+H70T+L73A+V77G+A78I+K141S+K142T+R143P+G144Y+L148A+L151A+A165I+Y130V+L163Q+K211H+F208R+S207I+T290S+A292G, MTTTEFANREFH+G69Y+H70T+L73A+V77G+A78I+K141S+K142T+R143P+G144Y+L148A+L151A+A165I+Y130M+L163R+K211H+F208R+S207I+T290S+A292G, MTTTEFANREFH+G69Y+H70T+L73A+V77G+A78I+K141S+K142T+R143P+G144Y+L148A+L151A+T152R+A165I+Y130M+L163Q+K211H+F208R+S207I+T290S+A292G, MTTTEFANREFH+G69Y+H70T+L73A+V77G+A78I+K141S+K142T+R143P+G144Y+S207 I1+T290S+A292G+A165I+Y130M+L163Q+K211H+F208R+L148A+L151A+T152R+M130V, MTTTEFANREFH+G69Y+H70T+L73A+V77G+A78I+K141T+K142S+R143P+G144Y+L148A+L151A+P167S+A165I+Y130M+L163Q+K211H+F208R+S207I+T290S+A292G, MTTTEFANREFH+G69Y+H70T+L73A+V77G+A78I+K141S+K142T+R143P+G144Y+L148A+L151A+T152R+A165I+Y130V+L163Q+K211H+F208R+R188L+S207I+T290S+A292G, MTTTEFANREIH+G69Y+H70T+L73A+V77G+A78I+K141S+K142T+R143P+G144Y+L148A+L151A+T152R+R188L+A165I+L163Q+Y130V+K211H+F208R+S207I+T290S+A292G+G17V+Q40H+T204S, MTTTEFANREFH+G69Y+H70T+L73A+V77G+A78I+K141S+K142T+R143P+G144Y+L148A+L151A+T152R+R188L+A165I+Y130V+L163Q+K211H+F208R+S207I+T290S+A292G+T 204S, MTTTEFANREIH+G17V+Q40H+T66M+G69Y+H70T+L73A+V77G+A78I+K141S+K142T+R143P+G144Y+A165I+Y130V+L163Q+L148A+L151A+T152R+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+E145S+Y130V+L148A+L151A+T152R+L163Q+A165I+R188L+T204S+S207I+F208R+K211H+T290S+A292G, MTTTEFANREFH+G17V+Q40H+T66M+G69Y+H70T+L73A+V77G+A78I+K141T+K142S+R143P+G144Y+K146R+E145G+Y130V+L148A+L151H+T152R+H153P+L163Q+A165I+R 188L+T204S+S207I+F208R+K211H+T290S+A292G, MTTTEFANREIH+G17V+Q40H+T66M+G69Y+H70T+L73A+V77G+A78I+K141S+K142T-R 143P+G144Y+A165I+Y130M+163Q+L148A+L151E+T152R+R188L+T204S+K211H+F208R+S207I+T290S+A292G, MTTTEFANREIH+G17V+Q40H+T204S+T66M+G69Y+H70T+L73A-V77G+A78I+K141S+K142T+R143P+G144Y+Y130V+L148A+L151H+T152R+H153P+L163Q+A165I+R188L+K211H+F2083R+S207I+T290S+A292G, MTTTEFANREFH+G17V+Q40H+T66M+G69Y+H70T+L73A+V77G+A78I+Y130M+K141S+K142T+R143P+G144Y+L148A+L151H+T152R+H153P+L163Q+A165I+R188L+T204S+K211H+F208R+S207I+T290S+A292G, MTTTEFANREIH+G17V+Q40H+T66M+G69Y+H70T+L73A+V77G+A78I+K141S+K142T-R 143P+G144Y+Y130V+L148A+L151E+T152R+L163Q+A165I+R188L+T204S+S207I+F208R+K211H+T290S+A292G, MTTTEFANREFH+G17V+Q40H+T66M+G69Y+H70T+L73A+V77G+A78I+K141S+K142T+R143P+G144Y+Y130V+L148A+L151H+T152R+H153P+L163Q+A165I+R188L+Y198F+T204S+F208R+S207I+K211H+T290S+A292G, MTTTEFANREIH+G17V+Q40H+T66Q+G69Y+

H70T+L73A+V77G+A78I+K141S+K142T+R143P+G144Y+Y130V+L148A+L151A+T152R+L163Q+A165I+R188L+T204S+K211H+F208R+S207I+T290S+A292G, MTTTEFANREFH+T66A+G69Y+H70T+L73A+V77G+A78I+K141S+K142T+R143P+G144Y+Y130V+L148A+L151A+T152R+L163Q+A165I+G187S+K211H+F208R+S207I+T290S+A292G, MTTTEFANREIH+G17V+Q40H+T66Q+G69Y+H70T+L73A+V77G+A78I+K141S+K142T+R143P+G144Y+Y130V+L148A+L151A+T152R+L163Q+A165I+R188L+K211H+F208R+T204S+S207I+T290S+A292G, MTTTEFANREIH+G17V+Q40H+G69Y+H70T+L73A+V77G+A78I+E105D+K141S+K142T+R143P+G144Y+Y130V+L148A+L151A+T152R+L163Q+A165+R1-88L+T204S+K211H+F208R+S207I+T290S+A292G, MTTTEFANREIH+G17V+Q40H+G69Y+H70T+L73A+V77G+A78I+K141S+K142T+R143P+G144Y+E145G+A165I+Y130V+L163Q+L148A+L151A+T152R+R188L+T204S+K211H+F208R+S207I+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151V+H153P+T152R+A165I+L163Q+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+S207I+V244M+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R, MTTTEFANREIH+G17V+Q40H+T66M+G69Y+H70T+L73A-V77G+A78I+K141S+K142T+R143P+G144Y+K146R+E145G+Y130M+L148A+L151H+T152R+H153P+I160F+L163Q+A165I+R188L+T204N+S207I+K211H+F208R+T290S+A292G, MTTTEFANREIH+G17V+Q40H+T66M+G69Y+H70T+L73A+V77G-A78I+K141S+K142T-R 143P+G144Y+K146R+E145G+Y130M+L148A+L151H+T152R+H153P+L163Q+A165I+R188L+T204N+K211H+F208R+S207I+T290S+A292G+V244E, MTTTEFANREIH+G17V+Q40H+T66M+G69Y+H70T+L73A+V77G+A78I+K141S+K142T+R143P+G144Y+Y130V+L148A+L151H+T152R+H153P+I160V+L163Q+A165I+R188L+T204 S+S207I+K211H+F208R+T290S+A292G, G17V+Q40H+T66M+G69Y+H70T+L73A+V77G+A78I+K141S+K142T+R143P+G144Y+K146R+E145G+Y130M+L148A+L151H+T152R+H153P+L163Q+A165I+R188L+T204S+S207I+K211H+208R+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+Y260F+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211Q+F208R+S207I+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+R273C, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+A242T+T290S+A292G+S278R+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+K150N+Y158N, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+V244M, MTTTEFANREIH+G17V-Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+Y158N. MTTTEFANREIH+G17V+Q40H+T66M+G69Y+H70T+L73A+V77G+A78I+K141S+K142T+R143P+G144Y+Y130M+L148A+L151H+T152R+H153P+L163Q-A165I+R188L+T204S+S207I+F208R+K211H+T290S+A292G+K146R+E145G+S278R, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+R273S, MTTTEFANREIH+G17V+Q40H+T66M+G69Y+H70T+L73A-V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+T3S+Y260F, MTTTEFANREIH+G17V+Q40H+T66M+G69Y+H70T+L73A+V77G+A78I+K141S K142T-R 143P+G144Y+Y130M+L148A+L151H+T152R+H153P+L163Q+A165I+R188L+T204S+S207I+F208R+1K211Q+T290S+A292G+K146R+E145G, MTTTEFANREIH+G17V+Q40H+T66M+G69Y+H70T+L73A-V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+I160F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+I160F+A242T, MTTTEFANREIH+G17V+Q40H+T66M+G69Y+H70T+L73A+V77G+A78I+K141S K142T-R 143P+G144Y+Y130M+L148A+L151H+T152R+H153P+L163Q+A165I+R188L+T204N+S207I+F208R+K211H+T290S+A292G+K146R+E145G+Y162F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+V244E, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+V244A, MTTTEFANREIH+G17V+Q40H+T66M+G69Y+H70T+L73A+V77G+A78I+K141S+K142T-R 143P+G144Y+Y130M+L148A+L151H+T152R+H153P+L163Q+A165I+R188L+T204N+S207I+F208R+K211H+T290S+A292G+K146R+E145G+Y260N+E261 D+F322Y, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+

R188L+T204N+S207I+F208R+K211H+T290S+A292G+K146R+E145G+Y260F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T134A, MTTTEFANREIH+G17V+Q40H+T66M+G69Y+H70T+L73A+V77G+A78I+K141S+K142T+R 143P+G144Y+Y130M+L148A+L151H+T152R+H153P+L163Q+A165I+R188L+T204N+S207I+F208R+K211H+T290S+A292G+K146R+E145G+S278R, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T270A+E282K, MTTTEFANREIH+G17V'Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T175A+R273C, MTTTEFANREIH+G17V+Q40H+T66M+G69Y+H70T+L73A+V77G+A78I+K141S+K142T+R143P+G144Y+Y130M+L148A+L151Q+T152R+H153P+L163Q+A165I+R188L+T204N+S207I+F208R+K211H+T290S+A292G+K146R+E145G, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+L237Q, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+R273T, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+D327M, MTTTEFANREIH+G17V+Q40H+T66M+G69Y+H70T+L73A-V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+V244H, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L1163Q+A165I+R188L+T204N+K211Q+F208R+S207I+T290S+A292G+S278R+R273T.

According to another aspect of the present disclosure, a DNA molecule is provided. The DNA molecule encodes the above transaminase mutant.

According to another aspect of the present disclosure, a recombinant plasmid is provided. The recombinant plasmid contains the DNA molecule.

Further, the recombinant plasmid is pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41 b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the present disclosure, a host cell is provided. The host cell contains any one of the above recombinant plasmids.

Further, the host cell includes a prokaryotic cell, yeast or a eukaryotic cell; preferably, the prokaryotic cell is an *E. coli* BL21 (DE3) cell or an *E. coli* Rosetta (DE3) cell.

According to another aspect of the present disclosure, a method for producing a chiral amine is provided. The method includes a step of catalyzing a transamination reaction of a ketone compound and an amino donor by a transaminase, and the transaminase is the above transaminase mutant.

Further, the ketone compound is

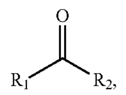

and a product of the transamination reaction is

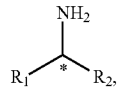

herein, $R_1$ and $R_2$ each independently represent an optionally substituted or unsubstituted alkyl, an optionally substituted or unsubstituted aralkyl, or an optionally substituted or unsubstituted aryl; and the $R_1$ and $R_2$ may be singly or combined with each other to form a substituted or unsubstituted ring.

Preferably, the $R_1$ and $R_2$ are an optionally substituted or unsubstituted alkyl having 1 to 20 carbon atoms, an optionally substituted or unsubstituted aralkyl, or an optionally substituted or unsubstituted aryl, more preferably an optionally substituted or unsubstituted alkyl having 1 to 10 carbon atoms, an optionally substituted or unsubstituted aralkyl, or an optionally substituted or unsubstituted aryl.

Preferably, the aryl includes a phenyl, a naphthyl, a pyridyl, a thienyl, an oxadiazolyl, an imidazolyl, a thiazolyl, a furyl, a pyrrolyl, a phenoxy, a naphthyloxy, a pyridyloxy, a thienyloxy, an oxadiazolyloxy, an imidazolyloxy, a thiazolyloxy, a furyloxy or a pyrrolyloxy.

Preferably, the alkyl includes a methyl, an ethyl, a propyl, a butyl, a pentyl, a hexyl, an isopropyl, a sec-butyl, a tert-butyl, a methoxy, an ethoxy, a tert-butoxy, a methoxycarbonyl, an ethoxycarbonyl, a tert-butoxycarbonyl, a vinyl, an allyl, a cyclopentyl or a cycloheptyl.

Preferably, the aralkyl is a benzyl.

Preferably, the substitution refers to substitution by a halogen atom, a nitrogen atom, a sulfur atom, a hydroxyl, a nitro group, a cyano group, a methoxy, an ethoxy, a carboxyl, a carboxymethyl, a carboxyethyl or a methylenedioxy.

Preferably, the ketone compound is

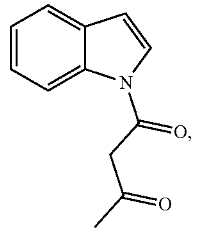

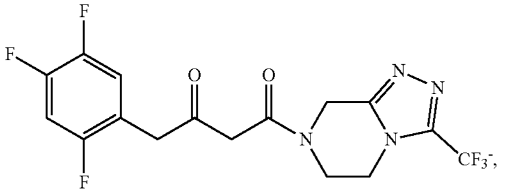

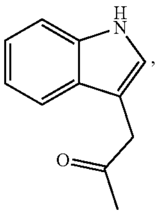

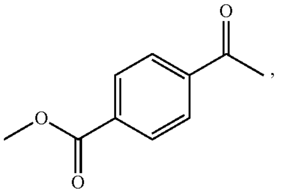

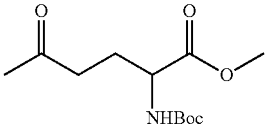

or

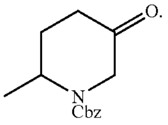

Further, the amino donor is isopropylamine or alanine, preferably isopropylamine.

Further, in a reaction system in which the transaminase catalyzes the transamination reaction of the ketone compound and the amino donor, a pH is 7-11, preferably 8-10, and more preferably 9-10; preferably, the temperature of the reaction system in which the transaminase catalyzes the transamination reaction of the ketone compound and the amino donor is 25° C.-60° C., more preferably 30-55° C., and further preferably 40-50° C.

The transaminase mutant of the present disclosure is based on the transaminase (SsTA protein) shown in SEQ ID NO:1, and is mutated through site-directed mutagenesis, as to change the amino acid sequence thereof, so the change of protein structures and functions is achieved. Through a directed screening method, the transaminase with the above mutation site is obtained. Therefore, a modified SsTA protein mutant acquires the catalytic activity on a carbonyl substrate, and the catalytic effect is better. On this basis, the modification is further performed, an obtained mutant is further verified for the catalytic activity on a sitagliptin precursor ketone, and the modification is further performed subsequently, the enzyme stability and tolerance are improved, the amount of enzymes used is reduced, and the difficulty of post-treatment is reduced, so that it is suitable for the industrial production.

DETAILED DESCRIPTION OF THE EMBODIMENTS

It should be noted that embodiments in the present application and features in the embodiments may be combined with each other in the case without conflicting. The present disclosure is described in detail below in combination with the embodiments.

SsTA is a transaminase derived from *Sciscionella* sp., it may catalyze the generation of a chiral amine from a carbonyl substrate, but it may not catalyze a substrate with a larger steric hindrance, such as a sitagliptin precursor ketone. The natural enzymes and modified enzymes has no catalytic activity on sitagliptin precursor ketone due to the larger steric hindrance thereof. At present, only ATA-117RD11 developed by Merck Company has this catalytic ability. Therefore, it is extremely challenged to develop an SsTA mutant to obtain the catalytic ability of a large-structure substrate, such as the sitagliptin precursor ketone.

The rational modification of enzymes is based on a three-dimensional molecular structure of the enzyme to modify a substrate binding site, a coenzyme binding site, a surface and other parts of the enzyme, as to change the catalytic properties of the enzyme and improve the activity and selectivity of the enzyme. The directed evolution of the enzymes is an irrational design of proteins, special evolutionary conditions are artificially created, a natural evolutionary mechanism is simulated, a gene is modified in vitro, and an error-prone Polymerase Chain Reaction (PCR), DNA shuffling and other technologies are applied, as to obtain an enzyme with expected properties in combination with an efficient screening system.

A technical scheme of the present disclosure rationally transforms the SsTA protein through a combination technology of rational design and random mutation, and an obtained mutant has an expanded substrate spectrum, and acquires the catalytic ability for the large-structure substrate; and at the same time, the stability thereof is enhanced, and it may be catalytic-reacted under conditions of a high concentration of a solvent and a high temperature.

The rational design may be performed by means of site-directed mutagenesis. Herein, site-directed mutagenesis: refers to the introduction of a desired change (usually a change representing a favorable direction), including addition, deletion, site mutation and the like of bases, into a target DNA fragment (may be a genome or a plasmid) by the PCR and other methods. The site-directed mutagenesis may quickly and efficiently improve the properties and representation of a target protein expressed by DNA, and is a very useful method in gene research.

A method of introducing the site-directed mutagenesis by using a whole-plasmid PCR is simple and effective, and is currently a more commonly used method. A principle thereof is that a pair of primers (forward and reverse) containing mutation sites are annealed with a template plasmid, and then "cyclic extended" with a polymerase. The so-called cyclic extension means that the polymerase extends the primers according to the template and returns to 5'-terminal of the primer after a circle, and then it undergoes a cycle of repeated heating and annealing and extending. This reaction is different from rolling circle amplification, and does not form a plurality of tandem copies. Extension products of the forward and reverse primers are annealed and matched to form an open-circle plasmid with a nick. An extension product is digested by Dpn I. Since the original template plasmid is derived from conventional *E. coli*, it is modified by dam methylation, and is fragmented because it is sensitive to the Dpn I. However, a plasmid with a mutated sequence synthesized in vitro is not digested because it is not methylated. Therefore, it may be successfully transformed in the subsequent transformation, namely a clone of a mutant plasmid may be obtained.

The mutant plasmid is transformed into an *E. coli* cell and overexpressed in the *E. coli*. Then, a crude enzyme is obtained by a method of ultrasonic cell-break. The best conditions for the induction of transaminase expression are as follows: it is induced overnight at 25° C. and 0.1 mM isopropyl-β-d-thiogalactoside (IPTG).

Software is used to perform the computer simulation analysis on a three-dimensional structure of the transaminase, and it is found that G69Y, H70T, L73A, V77G, V77S, V77T, A78I, Y130M, Y130V, Y130T, N132I, N132T, K141S, K142S, K142T, R143P, G144F, G144W, G144Y, E145D, E145S, E145G, K146R, L148A, L148I, L148T, L151A, L151H, L151E, L151V, L151Q, T152R, H153P, H153G, Y158S, 11600C, L1630, L163R, A165I, P167S, E170R, T175A, P180A, Y198F, S207I, T290S, T290G, A292G, Y198M, R216Q, R216E, R216S, S217N, W200A, F208R, F208L, and F208V are located near the center of the substrate activity, and the change thereof may effectively amplify a substrate binding pocket of SsTA, thereby the affinity of the enzyme to the substrate is improved. T66M, T66A, T660, T66S, E105D, T134A, K150N, G187S, R188L, Y158N, I160F, 1160L, I160V, Y162F, T204N, T204S, K211H, K211Q, L237Q, A242T, V244M, V244S, V244D, V244N, V244H, V244E, V244A, Y260F, Y260N, E261 D, T270A, R273S, R273C, R273T, S278R, E282K, and D327M may improve the stability of the enzyme.

The present disclosure modifies the SsTA protein, and performs an amino acid mutation on the protein through the rational design and directed evolution, through (G17V, L36P, Q40H, G69Y, H70T, L73A, V77G, V77S, V77T, A78I, Y130M. Y130V, Y130T, N132I, N132T, K141S, K142S, K142T, R143P, G144F, G144W, G144Y, E145D, E145S, E145G, K146R, L148A, L148I, L148T, L151A, L151H, L151E, L151V, L151Q, T152R, H153P, H153G, Y158S, 1160C, L163Q, L163R, A165I, P167S, E170R, T175A, P180A, Y198F, S207I, T290S, T290G, A292G, Y198M, R216Q, R216E, R216S, S217N, W200A, F208R, F208L, F208V) and other mutations, the catalytic activity of the enzyme is continuously improved, and through the method of directed evolution, T66M, T66A, T660, T66S, E105D, T134A, K150N, G187S, R188L Y158N, I160F, 1160L, I160V, Y162F T204N, T204S, K211H, K211Q. L237Q, A242T, V244M, V244S, V244D, V244N, V244H, V244E, V244A, Y260F, Y260N, E261D, T270A, R273S, R273Q, R273T, S278R, E282K, D327M and other sites are modified, as to continuously improve the stability of the enzyme.

In order to expand the substrate spectrum and catalytic activity of SsTA, the following substrates are selected as a substrate to verify the activity of a mutant obtained. A reaction formula is as follows:

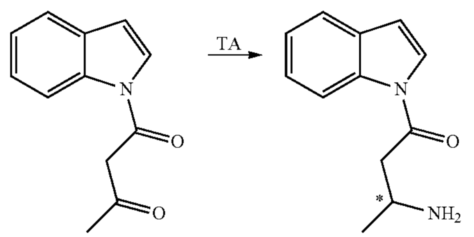

Strain information and experimental results are shown in Table 1.

TABLE 1

| Strain | Amino acid difference (compared to SsTA) | activity |
|---|---|---|
| M1 | SsTA | N.D. |
| M4 | G69Y + H70T + L73A + V77G + A78I + K141S + K142S + R143P + G144F + S207I + T290S + A292G | + |
| M6 | G69Y + H70T + L73A + V77G + A78I + Y130M + K141S + K142S + R143P + G144F + S207I + T290S + A292G | − |
| M7 | G69Y + H70T + L73A + V77G + A78I + K141S + K142S + R143P + G144F + S207I + T290S + A292G + A165I | ++ |
| M8 | G69Y + H70T + L73A + V77G + A78I + K141S + K142S + R143P + G144W + S207I + T290S + A292G + A165I + Y198M | +++ |
| M9 | G69Y + H70T + L73A + V77G + A78I + K141S + K142S + R143P + G144F + S207I + T290S + A292G + A165I + Y198M | +++ |
| M10 | G69Y + H70T + L73A + V77G + A78I + K141S + K142S + R143P + G144F + S207I + T290S + A292G + A165I + R216Q | +++ |
| M11 | G69Y + H70T + L73A + V77G + A78I + K141S + K142S + R143P + G144F + S207I + T290S + A292G + A165I + R216S | +++ |
| M12 | G69Y + H70T + L73A + V77G + A78I + K141S + K142S + R143P + G144F + S207I + T290S + A292G + A165I + Y198F | ++++ |
| M13 | G69Y + H70T + L73A + V77G + A78I + K141S + K142S + R143P + G144F + S207I + T290S + A292G + A165I + F208R | ++++ |
| M14 | G69Y + H70T + L73A + V77G + A78I + K141S + K142S + R143P + G144F + S207I + T290S + A292G + A165I + T204N | ++++ |
| M15 | G69Y + H70T + L73A + V77G + A78I + K141S + K142S + R143P + G144F + S207I + T290S + A292G + A165I + K211H | ++++ |
| M16 | G69Y + H70T + L73A + V77G + A78I + K141S + K142S + R143P + G144F + S207I + T290S + A292G + A165I + F144W + Y198F | ++++ |
| M17 | G69Y + H70T + L73A + V77G + A78I + K141S + K142S + R143P + G144W + S207I + T290S + A292G + A165I + Y198F + K211H | ++++ |

N.D. means that no product is detected,
+ means that a conversion rate of a product obtained using 10 wt wet cells is <50%,
− means that the conversion rate of the product obtained using 10 wt wet cells is <10%,
++ means that the conversion rate of the product obtained using 10 wt wet cells is >80% ,
+++ means that the conversion rate of the product obtained using 3 wt wet cells is <70%,
and ++++ means that the conversion rate of the product obtained using 3 wt wet cells is >70%.

SsTA has an amino acid sequence as shown in SEQ ID NO:1, SEQ ID NO: 1:

```
MTTTEFANSNLVAVEPGAIREPTPPGSVIQYSEYELDRSQPLAGGVAWIE

GEYVPADEARISIFDTGFGHSDLTYTVAHVWHGNIFRLEDHLDRLLHGAA

RLKLETGMSREELAGIAKRCVSLSQLREAYVNITITRGYGKKRGEKDLTK

LTHQVYVYAIPYLWAFPPEEQIFGTSVIVPRHVRRAGRNTIDPTIKNYQW

GDLTAASFEAKDRGARSAVLLDADNCVAEGPGFNVVLVKDGALVSPSRNA

LPGITRKTVYEIAAAKGIETMLRDVTSSELYEADELMAVTTAGGVTPITS

LDGEQVGNGEPGPITVAIRDRFWALMDEPSSLIEAIDY.
```

A modified SsTA protein mutant acquires the catalytic activity on the carbonyl substrate with a certain steric hindrance, and the catalytic effect is better. On this basis, the modification is further preformed, and the sitagliptin precursor ketone with the large steric hindrance is selected as a substrate to verify the activity, and the catalytic activity of SsTA is continuously expanded through methods such as site-directed mutagenesis, saturation mutagenesis, and directed evolution. Before the activity verification, 300 natural transaminases and mutants, including SsTA, are verified for the activity of the sitagliptin precursor ketone, and it is found that there is no catalytic activity, it is indicated that all of the natural transaminases do not have the catalytic activity on the sitagliptin precursor ketone because of the large steric hindrance thereof, even an existing mutant in our laboratory still has no catalytic activity. The modified SsTA mutant obtained by the further modification verifies the catalytic activity thereof on the sitagliptin precursor ketone. A reaction formula is as follows:

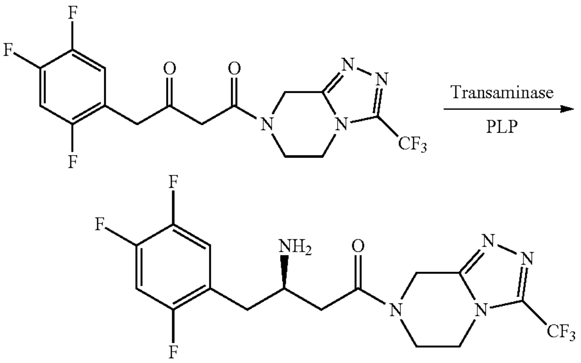

Strain information and experimental results are shown in Table 2.

TABLE 2

| Strain | Amino acid difference (compared to SsTA) | Activity |
|---|---|---|
| SsTA | N/A | ND |
| M18 | G69Y + H70T + L73A + V77G + A78I + K141S + K142S + R143P + G144F + S207I + A165I + Y130M + 163Q + T290S + A292G | – |
| M19 | G69Y + H70T + L73A + V77G + A78I + K141S + K142S + R143P + G144F + A165I + Y130M + L163Q + Y198F + S207I + T290S + A292G | – |
| M20 | G69Y + H70T + L73A + V77G + A78I + K141S + K142S + R143P + G144F + A165I + Y130M + L163Q + Y158S + I160C + N132T + S207I + T290S + A292G | – |
| M21 | G69Y + H70T + L73A + V77G + A78I + K141S + K142S + R143P + G144F + A165I + Y130M + L163Q + K211H + F208R + S207I + T290S + A292G | – |
| M22 | G69Y + H70T + L73A + V77G + A78I + K141S + K142S + R143P + G144F + A165I + Y130M + L163Q + Y158S + I160C + S207I + T290S + A292G | – |
| M23 | G69Y + H70T + L73A + V77G + A78I + K141S + K142T + R143P + G144F + A165I + Y130M + L163Q + K211H + F208R + S207I + T290S + A292G | – |
| M24 | G69Y + H70T + L73A + V77G + A78I + K141S + K142S + R143P + G144F + L148A + A165I + Y130M + L163Q + K211H + F208R + S207I + T290S + A292G | + |
| M25 | G69Y + H70T + L73A + V77G + A78I + K141S + K142S + R143P + G144F + L148I + A165I + Y130M + L163Q + K211H + F208R + S207I + T290S + A292G | – |
| M26 | G69Y + H70T + L73A + V77G + A78I + K141S + K142S + R143P + G144F + A165I + Y130M + L163Q + L151A + S207I + F208R + K211H + T290S + A292G | – |
| M27 | G69Y + H70T + L73A + V77G + A78I + K141S + K142S + R143P + G144F + P180A + A165I + Y130M + L163Q + F208R + S207I + K211H + T290S + A292G | – |
| M28 | G69Y + H70T + L73A + V77G + A78I + K141S + K142T + R143P + G144F + L148A + L151A + A165I + Y130M + L163Q + K211H + F208R + S207I + T290S + A292G | + |
| M29 | G69Y + H70T + L73A + V77G + A78I + K141S + K142T + R143P + G144F + L148A + L151A + A165I + Y130M + L163R + K211H + F208R + S207I + T290S + A292G | + |
| M30 | MTTTEFANREFH + G69Y + H70T + L73A + V77G + A78I + K141S + K142T + R143P + G144Y + L148A + L151A + A165I + Y130M + L163Q + K211H + F208R + S207I + T290S + A292G | + |
| M31 | G69Y + H70T + L73A + V77G + A78I + Y130V + K141S + K142T + R143P + G144F + E145D + L148T + L151A + A165I + LL163Q + F208R + S207I + K211H + T290S + A292G | + |
| M32 | MTTTEFANREFH + G69Y + H70T + L73A + V77G + A78I + K141S + K142T + R143P + G144Y + L148A + L151A + Y130T + L163Q + A165I + K211H + F208R + S207I + T290S + A292G | ++ |
| M33 | MTTTEFANREFH + G69Y + H70T + L73A + V77G + A78I + K141S + K142T + R143P + G144Y + L148A + L151A + A165I + Y130V + L163Q + K211H + F208R + S207I + T290S + A292G | ++ |
| M34 | MTTTEFANREFH + G69Y + H70T + L73A + V77G + A78I + K141S + K142T + R143P + G144Y + L148A + L151A + A165I + Y130M + L163R + K211H + F208R + S207I + T290S + A292G | ++ |
| M35 | MTTTEFANREFH + G69Y + H70T + L73A + V77G + A78I + K141S + K142T + R143P + G144Y + L148A + L151A + T152R + A165I + Y130M + L163Q + K211H + F208R + S207I + T290S + A292G | ++ |
| M36 | MTTTEFANREFH + G69Y + H70T + L73A + V77G + A78I + K141S + K142T + R143P + G144Y + S207I + T290S + A292G + A165I + Y130M + L163Q + K211H + F208R + L148A + L151A + T152R + M130V | ++ |

TABLE 2-continued

| Strain | Amino acid difference (compared to SsTA) | Activity |
|---|---|---|
| M37 | MTTTEFANREFH + G69Y + H70T + L73A + V77G + A78I + K141T + K142S + R143P + G144Y + L148A + L151A + P167S + A165I + Y130M + L163Q + K211H + F208R + S207I + T290S + A292G | ++ |
| M38 | MTTTEFANREFH + G69Y + H70T + L73A + V77G + A78I + K141S + K142T + R143P + G144Y + L148A + L151A + T152R + A165I + Y130V + L163Q + K211H + F208R + R188L + S207I + T290S + A292G | ++ |
| M39 | MTTTEFANREIH + G69Y + H70T + L73A + V77G + A78I + K141S + K142T + R143P + G144Y + L148A + L151A + T152R + R188L + A165I + L163Q + Y130V + K211H + F208R + S207I + T290S + A292G + G17V + Q40H + T204S | ++ |
| M40 | MTTTEFANREFH + G69Y + H70T + L73A + V77G + A78I + K141S + K142T + R143P + G144Y + L148A + L151A + T152R + R188L + A165I + Y130V + L163Q + K211H + F208R + S207I + T290S + A292G + T204S | ++ |
| M41 | MTTTEFANREIH + G17V + Q40H + T66M + G69Y + H70T + L73A + V77G + A78I + K141S + K142T + R143P + G144Y + A165I + Y130V + L163Q + L148A + L151A + T152R + R188L + T204S + S207I + K211H + F208R + T290S + A292G | +++ |
| M42 | MTTTEFANREIH + G17V + Q40H + T66M + G69Y + H70T + L73A + V77G + A78I + K141S + K142T + R143P + G144Y + E145S + Y130V + L148A + L151A + T152R + L163Q + A165I + R188L + T204S + S207I + F208R + K211H + T290S + A292G | ++++ |
| M43 | MTTTEFANREFH + G17V + Q40H + T66M + G69Y + H70T + L73A + V77G + A78I + K141T + K142S + R143P + G144Y + K146R + E145G + Y130V + L148A + L151H + T152R + H153P + L163Q + A165I + R188L + T204S + S207I + F208R + K211H + T290S + A292G | ++++ |
| M44 | MTTTEFANREIH + G17V + Q40H + T66M + G69Y + H70T + L73A + V77G + A78I + K141S + K142T + R143P + G144Y + A165I + Y130M + 163Q + L148A + L151E + T152R + R188L + T204S + K211H + F208R + S207I + T290S + A292G | ++++ |
| M45 | MTTTEFANREIH + G17V + Q40H + T204S + T66M + G69Y + H70T + L73A + V77G + A78I + K141S + K142T + R143P + G144Y + Y130V + L148A + L151H + T152R + H153P + L163Q + A165I + R188L + K211H + F208R + S207I + T290S + A292G | ++++ |
| M46 | MTTTEFANREFH + G17V + Q40H + T66M + G69Y + H70T + L73A + V77G + A78I + Y130M + K141S + K142T + R143P + G144Y + L148A + L151H + T152R + H153P + L163Q + A165I + R188L + T204S + K211H + F208R + S207I + T290S + A292G | ++++ |
| M47 | MTTTEFANREIH + G17V + Q40H + T66M + G69Y + H70T + L73A + V77G + A78I + K141S + K142T + R143P + G144Y + Y130V + L148A + L151E + T152R + L163Q + A165I + R188L + T204S + S207I + F208R + K211H + T290S + A292G | ++++ |
| M48 | MTTTEFANREFH + G17V + Q40H + T66M + G69Y + H70T + L73A + V77G + A78I + K141S + K142T + R143P + G144Y + Y130V + L148A + L151H + T152R + H153P + L163Q + A165I + R188L + Y198F + T204S + F208R + S207I + K211H + T290S + A292G | ++++ |
| M50 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + T204S + K211H + F208R + S207I + T290S + A292G | ++++ |
| M51 | MTTTEFANREFH + T66A + G69Y + H70T + L73A + V77G + A78I + K141S + K142T + R143P + G144Y + Y130V + L148A + L151A + T152R + L163Q + A165I + G187S + K211H + F208R + S207I + T290S + A292G | ++ |
| M52 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + K211H + F208R + T204S + S207I + T290S + A292G | +++ |
| M53 | MTTTEFANREIH + G17V + Q40H + G69Y + H70T + L73A + V77G + A78I + E105D + K141S + K142T + R143P + G144Y + Y130V + L148A + L151A + T152R + L163Q + A165I + R188L + T204S + K211H + F208R + S207I + T290S + A292G | +++ |
| M54 | MTTTEFANREIH + G17V + Q40H + G69Y + H70T + L73A + V77G + A78I + K141S + K142T + R143P + G144Y + E145G + A165I + Y130V + L163Q + L148A + L151A + T152R + R188L + T204S + K211H + F208R + S207I + T290S + A292G | +++ |
| M55 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G | +++++ |
| M56 | MTTTEFANREIH + G17V + Q40H + T66M + G69Y + H70T + L73A + V77G + A78I + K141S + K142T + R143P + G144Y + Y130M + K146R + E145G + L148A + L151V + H153P + T152R + A165I + L163Q + R188L + T204S + S207I + K211H + F208R + T290S + A292G | +++++ |
| M57 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + S207I + V244M + K211H + F208R + T290S + A292G | ++++++ |
| M58 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R | ++++++ |
| M59 | MTTTEFANREIH + G17V + Q40H + T66M + G69Y + H70T + L73A + V77G + A78I + K141S + K142T + R143P + G144Y + K146R + E145G + Y130M + L148A + L151H + T152R + H153P + I160F + L163Q + A165I + R188L + T204N + S207I + K211H + F208R + T290S + A292G | ++++++ |
| M60 | MTTTEFANREIH + G17V + Q40H + T66M + G69Y + H70T + L73A + V77G + A78I + K141S + K142T + R143P + G144Y + K146R + E145G + Y130M + L148A + L151H + T152R + H153P + L163Q + A165I + R188L + T204N + K211H + F208R + S207I + T290S + A292G + V244E | ++++++ |

TABLE 2-continued

| Strain | Amino acid difference (compared to SsTA) | Activity |
|---|---|---|
| M61 | MTTTEFANREIH + G17V + Q40H + T66M + G69Y + H70T + L73A + V77G + A78I + K141S + K142T + R143P + G144Y + Y130V + L148A + L151H + T152R + H153P + I160V + L163Q + A165I + R188L + T204S + S207I + K211H + F208R + T290S + A292G | ++++++ |
| M62 | G17V + Q40H + T66M + G69Y + H70T + L73A + V77G + A78I + K141S + K142T + R143P + G144Y + K146R + E145G + Y130M + L148A + L151H + T152R + H153P + L163Q + A165I + R188L + T204S + S207I + K211H + F208R + T290S + A292G + S278R | ++++++ |
| M84 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + Y260F + T290S + A292G + S278R | ++++++ |
| M85 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211Q + F208R + S207I + T290S + A292G + S278R | ++++++ |
| M86 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + R273C | ++++++ |
| M87 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + A242T + T290S + A292G + S278R + R273C | ++++++ |
| M88 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + R273T | ++++++ |
| M89 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + D327M | ++++++ |
| M90 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + V244H | ++++++ |
| M91 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211Q + F208R + S207I + T290S + A292G + S278R + R273T | ++++++ |

ND means that no product is detected in a catalytic reaction using >10 wt wet cells,
− means that the conversion rate of the product obtained using 10 wt wet cells is <10%,
+ means that the conversion rate of the product obtained using 10 wt wet cells is 10%-30%,
++ means that the conversion rate of the product obtained using 10 wt wet cells is 40%-70%
+++ means that the conversion rate of the product obtained using 10 wt wet cells is 70%-90%,
++++ means that the conversion rate of the product obtained using 10 wt wet cells is >90%,
+++++ means that the conversion rate of the product obtained using 5 wt wet cells is >90%,
and ++++++ means that the conversion rate of the product obtained using 3 wt wet cells is >90%.
"MTTTEFANREFH" and "MTTTEFANREIH" are amino acid sequences added at an N-terminus of SEQ ID NO: 1.

After the modification of the site-directed mutagenesis and directed evolution, the mutant acquires the ability to catalyze the substrate with the larger steric hindrance, and the activity is continuously gradually improved. In order to further improve the stability performance of the mutant, the tolerance of the mutant is modified through the error-prone PCR and directed screening methods.

A random mutant gene is obtained by the error-prone PCR, and the gene containing the random mutation is constructed on a pET22b vector, and transformed into BL21 (DE3) host bacteria, as to construct a mutant strain library. After being identified by sequencing, the mutation frequency is adjusted to maintain about 1-3 amino acid mutations in each target protein. The mutant library is induced to obtain the protein, the sitagliptin precursor ketone is used as a screening substrate, and the mutants are screened by setting different temperatures and solvent tolerance conditions. The strains obtained by screening are sequenced and re-verified to confirm beneficial mutants, as shown specifically in Table 3.

TABLE 3

| Strain | Amino acid difference (compared to SsTA) | Increased residual activity |
|---|---|---|
| M63 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + K150N + Y158N | +[1] |
| M64 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + V244M | ++[1] |

TABLE 3-continued

| Strain | Amino acid difference (compared to SsTA) | Increased residual activity |
|---|---|---|
| M65 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + Y158N | ++[1] |
| M66 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + S278R | +[1] |
| M67 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + R273S | +[1] |
| M68 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + T3S + Y260F | +[1] |
| M69 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211Q + T290S + A292G + K146R + E145G | +[1] |
| M70 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204S + S207I + F208R + K211H + T290S + A292G + K146R + E145G + I160F | +[2] |
| M71 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + I160F + A242T | +[2] |
| M72 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + Y162F | ++[2] |
| M73 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + V244E | +++[2] |
| M74 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + V244A | +++[2] |
| M75 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + Y260N + E261D + F322Y | +[2] |
| M76 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + Y260F | ++[2] |
| M77 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + T134A | ++[2] |
| M78 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + S278R | ++[2] |
| M79 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + T270A + E282K | ++[2] |
| M80 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + R273C | ++[2] |
| M81 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + T175A + R273C | ++[2] |
| M82 | MTTTEFANREIH + G17V + Q40H + T66M + G69Y + H70T + L73A + V77G + A78I + K141S + K142T + R143P + G144Y + Y130M + L148A + L151Q + T152R + H153P + L163Q + A165I + R188L + T204N + S207I + F208R + K211H + T290S + A292G + K146R + E145G | ++[2] |

TABLE 3-continued

| Strain | Amino acid difference (compared to SsTA) | Increased residual activity |
|---|---|---|
| M83 | MTTTEFANREIH + G17V + Q40H + T66M + G69Y + H70T + L73A + V77G + A78I + K141S + K142T + R143P + G144Y + Y130M + L148A + L151H + T152R + H153P + L163Q + A165I + R188L + T204N + S207I + F208R + K211H + T290S + A292G + K146R + E145G + L237Q | +[2] |

+[1] means that after 45° C. and 25% dimethylsulfoxide (DMSO) tolerant treatment for 1 h, the residual activity is increased by 0.1-1 time,
++[1] means that after 45° C. and 25% DMSO tolerant treatment for 1 h, the residual activity is increased by 1-2 times,
+[2] means that after 55° C. and 25% DMSO tolerant treatment for 1 h, the residual activity is increased by 1-2 times,
++[2] means that after 55° C. and 25% DMSO tolerant treatment for 1 h, the residual activity is increased by 2-3 times,
and +++[2] means that after 55° C. and 25% DMSO tolerant treatment for 1 h, the residual activity is increased by 3-4 times.
The mutant has an ee value of 95%-99% after selective determination.

The tolerance-modified mutant is verified with the sitagliptin precursor ketone as a substrate. The optimal reaction temperature for M19 is 30° C., the optimal reaction temperature for M38, M41 and other mutants is increased to 35° C., and the optimal reaction temperature for M57, M58, M60, M72, and M76 is increased to 55° C. At the same time, the stability of the mutant in the solvent is also significantly improved, and the optimal reaction DMSO concentration is increased from 5% to 30%.

According to a typical embodiment of the present disclosure, a transaminase mutant is provided. An amino acid sequence of the transaminase mutant is an amino acid sequence obtained by a mutation of an amino acid sequence shown in SEQ ID NO:1, and the mutation at least includes one of the following mutation sites: G17V, L36P, 040H, G69Y, H70T, L73A, V77G, V77S, V77T, A78I, Y130M, Y130V, Y130T, N132I, N132T, K141S, K142S, K142T, R143P, G144F, G144W, G144Y, E145D, E145S, E145G, K146R, L148A, L148I, L148T, L151A, L151H, L151E, L151V, L151Q, T152R, H153P, H153G, Y158S, 1160C, L163Q, L163R, A165I, P167S, E170R, T175A, P180A, Y198F, S207I, T290S, T290G, A292G, Y198M, R216Q, R216E, R216S, S217N, W200A, F208R, F208L and F208V. Preferably, the mutation at least includes one of the following mutation sites: T66M, T66A, T66Q, T66S, E105D, T134A, K150N, G187S, R188L, Y158N, I160F, I160L, I160V, Y162F, T204N, T204S, K211H, K211Q, L237Q, A242T, V244M, V244S, V244D, V244N, V244H, V244E, V244A, Y260F, Y260N, E261 D, T270A, R273S, R273C, R273T, S278R, E282K and D327M; or the amino acid sequence of the transaminase mutant has the mutation site in the mutated amino acid sequence, and has more than 80% identity with the mutated amino acid sequence.

The transaminase mutant of the present disclosure is based on the transaminase (SsTA protein) shown in SEQ ID NO:1, and is mutated through site-directed mutagenesis, as to change the amino acid sequence thereof, so the change of protein structures and functions is achieved. Through a directed screening method, the transaminase with the above mutation site is obtained. Therefore, a modified SsTA protein mutant acquires the catalytic activity on a carbonyl substrate, and the catalytic effect is better. On this basis, the modification is further performed, an obtained mutant is further verified for the catalytic activity on a sitagliptin precursor ketone, and the modification is further performed subsequently, the enzyme stability and tolerance are improved, the amount of enzymes used is reduced, and the difficulty of post-treatment is reduced, so that it is suitable for the industrial production.

A term "identity" used herein has the meaning generally known in the field, and those skilled in the art are also familiar with rules and standards for determining the identity between different sequences. The sequence defined by the present disclosure with different degrees identity must also have the improved tolerance to the organic solvent by the transaminase. In the above embodiment, preferably the amino acid sequence of the transaminase mutant has the above identity and has or encodes an amino acid sequence with the improved tolerance to the organic solvent. Those skilled in the art may obtain such a variant sequence under the teaching of the disclosure of the present application.

Preferably, the mutation at least includes one of the following mutation site combinations: L73A+V77G+T290S, H70T+L73A+V77G+A78I+K141S+R143P+S207I+T290S+A292G or H70T+L73A+V77G+G144F/Y/W+S207I.

More preferably, the mutation at least includes one of the following mutation site combinations: G69Y+H70T+L73A+V77G+A78I+K141S+K142S+143P+G144F+S207I+T290S+A292G, G69Y+H70T+L73A+V77G+A78I+K141S+K142S+R143P+G144F+S207I+T290S+A292G+A165I, G69Y+H70T+L73A+V77G+A78I+K141S+K142S+R143P+G144W+S207I+T290S+A292G+A165I+Y198M, G69Y+H70T+L73A+V77G+A78I+K141S+K142S+R143P+G144F+S207I+T290S+A292G+A165I+Y198M, G69Y+H70T+L73A+V77G+A78I+K141S+K142S+R143P+G144F+S207I+T290S+A292G+A165I+R216Q, G69Y+H70T+L73A+V77G+A78I+K141S+K142S+R143P G144F+S207I+T290S+A292G+A165I+R216S, G69Y+H70T+L73A+V77G+A78I+K141S+K142S+R143P+G144F+S207I+T290S+A292G+A165I+Y198F, G69Y+H70T+L73A+V77G+A78I+K141S+K142S+R143P+G144F+S207I+T290S+A292G+A165I+F208R, G69Y+H70T+L73A+V77G+A78I+K141S+K142S+R143P+G144F+S207I+T290S+A292G+A165I+T204N, G69Y+H70T+L73A+V77G+A78I+K141S+K142S+R143P+G144F+S207I+T290S+A292G+A165I+K211H, G69Y+H70T+L73A+V77G+A78I+K141S+K142S+R143P+G144F+S207I+T290S+A292G+A165I+F144W+Y198F, G69Y+H70T+L73A+V77G+A78I+K141S+K142S+R143P+G144W+S207I+T290S+A292G+A165I+Y198F+K211H, G69Y+H70T+L73A+V77G+A78I+K141S+K142S+R143P G144F+S207I+A165I+Y130M+163Q+T290S+A292G, G69Y+H70T+L73A+V77G+A78I+K141S+K142S+R143P+G144F+A165+Y130M+L163Q+Y198F+S207I+T290S+A292G, G69Y+H70T+L73A+V77G+A78I+K141S+K142S+R143P+G144F+A165I+Y130M+L1630+Y158S+I160C+N132T+S207I+T290S+A292G, G69Y+H70T+L73A+V77G+A78I+K141S+K142S+R143P+G144F+A165I+Y130M+L163Q+K211H+F208R+S207I+T290S+A292G, G69Y+H70T+L73A+V77G+A78I+K141S+K142S+R143P+G144F+

A165I+Y130M+L1630+Y158S+1160C+S207I+T290S+A292G, G69Y+H70T+L73A+V77G+A78I+K141S+K142T+R143P+G144F+A165I Y130M+L163Q+K211H+F208R+S207I+T290S+A292G, G69Y+H70T+L73A+V77G+A78I+K141S+K142S+R143P+G144F+L148A+A165+Y130M+L163Q+K211H+F208R+S207I+T290S+A292G, G69Y+H70T+L73A+V77G+A78I+K141S+K142S+R143P+G144F+L148I+A165I+Y130M+L163Q+K211H+F208R+S207I+T290S+A292G, G69Y+H70T+L73A+V77G+A78I+K141S+K142S+R143P+G144F+A165I+Y130M+L1630L151A+S207I+F208R+K211H+T290S+A292G, G69Y+H70T+L73A+V77G+A78I+K141S+K142S+R143P+G144F+P180A+A165I+Y130M+L163Q+F208R+S207I+K211H+T290S+A292G, G69Y+H70T+L73A+V77G+A78I+K141S+K142T+R143P+G144F+L148A+L151A+A165I+Y 130M+L163Q+K211H+F208R+S207I+T290S+A292G, G69Y+H70T+L73A+V77G+A78I+K141S+K142T+R143P+G144F+L148A+L151A+A165I+Y 130M+L163R+K211H+F208R+S207I+T290S+A292G, MTTTEFANREFH+G69Y+H70T+L73A+V77G+A78I+K141S+K142T+R143P+G144Y+L148A+L151A+A165I+Y130M+L163Q+K211H+F208R+S207I+T290S+A292G, G69Y+H70T+L73A+V77G+A78I+Y30V+K141S+K142T+R143P+G144F+E145D+L148T+L151A+A165I+LL163Q+F2083R+S207I+K211H+T290S+A292G, MTTTEFANREFH+G69Y+H70T+L73A+V77G+A78I+K141S+K142T+R143P+G144Y+L148A+L151A+Y130T+L163Q+A165I+K211H+F208R+S207I+T290S+A292G. MTTTEFANREFH+G69Y+H70T+L73A+V77G+A78I+K141S+K142T+R143P+G144Y+L148A+L151A+A165I+Y130V+L163Q+K211H+F208R+S207I+T290S+A292G, MTTTEFANREFH+G69Y+H70T+L73A+V77G+A78I+K141S+K142T+R143P+G144Y+L148A+L151A+A165+Y130M+L163R+K211H+F208R+S207I+T290S+A292G, MTTTEFANREFH+G69Y+H70T+L73A+V77G+A78I+K141S+K142T+R143P+G144Y+L148A+L151A+T152R+A165I+Y130M+L163Q+K211H+F208R+S207I+T290S+A292G, MTTTEFANREFH+G69Y+H70T+L73A+V77G+A78I+K141S+K142T+R143P+G144Y+S207 I1+T290S+A292G+A1165+Y130M+L163Q+K211H+F208R+L148A+L151A+T152R+M130V, MTTTEFANREFH+G69Y+H70T+L73A+V77G+A78I+K141 T+K142S+R143P+G144Y+L148A+L151A+P167S+A165I+Y130M+L163Q+K211H+F208R+S207I+T290S+A292G, MTTTEFANREFH+G69Y+H70T+L73A+V77G+A78I+K141S+K142T+R143P+G144Y+L148A+L151A+T152R+A165I+Y130V+L163Q+K211H+F208R+R188L+S207I+T290S+A292G, MTTTEFANREIH+G69Y+H70T+L73A+V77G+A78I+K141S+K142T+R143P+G144Y+L148A+L151A+T152R+R188L+A165I+L163Q+Y130V+K211H+F208R+S207I+T290S+A292G+G17V+Q40H+T204S, MTTTEFANREFH+G69Y+H70T+L73A+V77G+A78I+K141S+K142T+R143P+G144Y+L148A+L151A+T152R+R188L+A165I+Y130V+L163Q+K211H+F208R+S207I+T290S+A292G+T 204S, MTTTEFANREIH+G17V+Q40H+T66M+G69Y+H70T+L73A+V77G+A78I+K141S+K142T+R143P+G144Y+A165I+Y130V+L163Q+L148A+L151A+T152R+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+E145S+Y130V+L148A+L151A+T152R+L163Q+A165I+R188L+T204S+S207I+F208R+K211H+T290S+A292G, MTTTEFANREFH+G17V+040H+T66M+G69Y+H70T+L73A+V77G+A78I+K141T+K142S+R143P+G144Y+K146R+E145G+Y130V+L148A+L151H+T152R+H153P+L163Q+A165I+R 188L+T204S+S207I+F208R+K211H+T290S+A292G, MTTTEFANREIH+G17V+Q40H+T66M+G69Y+H70T+L73A+V77G+A78I+K141S+K142T+R143P+G144Y+A165I+Y130M+163Q+L148A+L151E+T152R+R188L+T204S+K211H+F208R+S207I+T290S+A292G, MTTTEFANREIH+G17V+Q40H+T204S+T66M+G69Y+H70T+L73A+V77G+A78I+K141S+K142T+R143P+G144Y+Y130V+L148A+L151H+T152R+H153P+L163Q+A165I+R188L+K211H+F208R+S207I+T290S+A292G, MTTTEFANREFH+G17V+040H+T66M+G69Y+H70T+L73A+V77G+A78I+Y130M+K141S+K142T+R143P+G144Y+L148A+L151H+T152R+H153P+L163Q+A165I+R188L+T204S+K211H+F208R+S207I+T290S+A292G, MTTTEFANREIH+G17V+Q40H+T66M+G69Y+H70T+L73A-V77G+A78I+K141S+K142T+R143P+G144Y+Y130V+L148A+L151E+T152R+L163Q+A165I+R188L+T204S+S207I+F208R+K211H+T290S+A292G, MTTTEFANREFH+G17V+Q40H+T66M+G69Y+H70T+L73A+V77G+A78I+K141S+K142T R143P+G144Y+Y130V+L148A+L151H+T152R+H153P+L163Q+A165I+R188L+Y198F+T204S+F208R+S207I+K211H+T290S+A292G, MTTTEFANREIH+G17V+Q40H+T66Q+G69Y+H70T+L73A+V77G+A78I+K141S+K142T+R143P+G144Y+Y130V+L148A+L151A+T152R+L163Q+A165I+R188L+T204S+K211H+F208 R+S207I+T290S+A292G, MTTTEFANREFH+T66A+G69Y+H70T+L73A+V77G+A78I+K141S+K142T+R143P+G144Y+Y130V+L148A+L151A+T152R+L163Q+A165I+G187S+K211H+F208R+S207I+T290S+A292G, MTTTEFANREIH+G17V+Q40H+T66Q+G69Y+H70T+L73A+V77G+A78I+K141S+K142T+R143P+G144Y+Y130V+L148A+L151A+T152R+L163Q+A165I+R188L+K211H+F208R+T204S+S207I+T290S+A292G, MTTTEFANREIH+G17V+040H+G69Y+H70T+L73A+V77G+A78I+E105D+K141S+K142T+R143P+G144Y+Y130V+L148A+L151A+T152R+L163Q+A165I+R188L+T204S+K211H+F208R+S207I+T290S+A292G, MTTTEFANREIH+G17V'Q40H+G69Y+H70T+L73A+V77G+A78I+K141S+K142T+R143P+G144Y+E145G+A165I+Y130V+L163Q+L148A+L151A+T152R+R188L+T204S+K211H+F208R+S207I+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G. MTTTEFANREIH+G17V+Q40H+T66M+G69Y+H70T+L73A+V77G+A78I+K141S+K142T+R143P+G144Y+Y130M+K146R+E145G+L148A+L151V+H153P+T152R+A165I+L163Q+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+S207I+V244M+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R, MTTTEFANREIH+G17V+Q40H+T66M+G69Y+H70T+L73A+V77G+A78I+K141S+K142T+R143P+G144Y+K146R+E145G+Y130M+L148A+L151H+T152R+H153P+I160F+L163Q+A165I+R188L+T204N+S207I+K211H+F208R+T290S+A292G, MTTTEFANREIH+G17V+Q40H+T66M+G69Y+H70T+L73A+V77G+A78I+K141S+K142T+R143P+G144Y+K146R+E145G+Y130M+L148A+L151H+T152R+H153P+L163Q+A165I+R188L+T204N+K211H+F208R+S207I+T290S+A292G+V244E, MTTTEFANREIH+G17V+Q40H+T66M+G69Y+H70T+L73A+V77G+A78I+K141S+K142T+R143P+G144Y+

Y130V+L148A+L151H+T152R+H153P+I160V+L163Q+A165I+R188L+T204S+S207I+K211H+F208R+T290S+A292G, G17V+Q40H+T66M+G69Y+H70T+L73A+V77G+A78I+K141S+K142T+R143P+G144Y+K146R+E145G+Y130M+L148A+L151H+T152R+H153P+L163Q+A165I+R188L+T204S+S207I+K211H+F208R+290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+Y260F+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211Q+F208R+S207I+T290S+A292G+S278R, MTTTEFANREIH+G17V+Q40H+T66M+G69Y+H70T+L73A+V77G+A78I+K141S+K142T-R 143P+G144Y+Y130M+K146R+E145G+L148A+L151H+T152R+H153P+L163Q+A165I+R188L+T204N+K211H+F208R+S207I+T290S+A292G+S278R+R273C, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+A242T+T290S+A292G+S278R+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+K150N+Y158N, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+V244M, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+Y158N, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+S278R, MTTTEFANREIH+G17V+Q40H+T66M+G69Y+H70T+L73A+V77G+A78I+K141S+K142T+R 143P+G144Y+Y130M+L148A+L151H+T152R+H153P+L163Q+A165I+R188L+T204S+S207I+F208R+K211H+T290S+A292G+K146R+E145G+R273S, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+T3S+Y260F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211Q+T290S+A292G+K146R+E145G, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+I160F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+I160F+A242T, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+Y162F, MTTTEFANREIH+G17V+Q40H+T66M+G69Y+H70T+L73A+V77G+A78I+K141S+K142T+R143P+G144Y+Y130M+L148A+L151H-T152R+H153P+L163Q+A165I+R188L+T204N+S207I+F208R+K211H+T290S+A292G+K146R+E145G+V244E, MTTTEFANREIH+G17V+Q40H+T66M+G69Y+H70T+L73A+V77G+A78I+K141S+K142T+R143P+G144Y+Y130M+L148A+L151H+T152R+H153P+L163Q-A165I+R188L+T204N+S207I+F208R+K211H+T290S+A292G+K146R+E145G+V244A, MTTEFANREIH+G17V+Q40H+T66M+G69Y+H70T+L73A-V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+Y260N+E261 D-F322Y, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+Y260F, MTTTEFANREIH+G17V+Q40H+T66M+G69Y+H70T+L73A+V77G+A78I+K141S+K142T+R143P+G144Y+Y130M+L148A+L151H+T152R+HH153P+L163Q+A165I+R188L+T204N+S20 7I+F208R+K211H+T290S+A292G+K146R+E145G+T134A, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+S278R, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T270A+E282K, MTTTEFANREIH+G17V+Q40H+T66M+G69Y+H70T+L73A+V77G+A78I+K141S+K1I42T+R143P+G144Y+Y130M+L148A+L151H+T152R+H153P+L163Q+A165I+R188L+T204N+S207I+F208R+K211H+T290S+A292G+K146R+E145G+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T175A+R273C, MTTTEFANREIH+G17V+Q40H+T66M+G69Y+H70T+L73A+V77G+A78I+K141S+K142T+R143P+G144Y+Y130M+L148A+L151Q+T152R+H153P+L163Q+A165I+R188L+T204N+S207I+F208R+K211H+T290S+A292G+K146R+E145G, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+L237Q. MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I-T290S+A292G+S2783R+R273T, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+D327M, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211I H+F208R+S207I+T290S+A292G+S278R+V244H,

MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211Q+F208R+S207I+T290S+A292G+S278R+R273T.

According to a typical embodiment of the present disclosure, a DNA molecule is provided. The DNA molecule encodes the above transaminase mutant. The above transaminase mutant encoded by the DNA molecule acquires the catalytic activity on the carbonyl substrate, and the catalytic effect is better. Some of the mutants also acquire the catalytic activity on the sitagliptin precursor ketone, and improve the stability and tolerance of the enzyme, the amount of the enzyme used is reduced, and the difficulty of post-treatment is reduced, so that it is suitable for the industrial production.

The above DNA molecule of the present disclosure may also exist in the form of an "expression cassette". The "expression cassette" refers to a linear or circular nucleic acid molecule, covering DNA and RNA sequences that may direct the expression of a specific nucleotide sequence in an appropriate host cell. Generally speaking, it includes a promoter operatively linked to a target nucleotide, and it is optionally operatively linked to a termination signal and/or other regulatory elements. The expression cassette may also include a sequence required for proper translation of the nucleotide sequence. A coding region usually encodes a target protein, but also encodes a target functional RNA in a sense or antisense direction, such as an antisense RNA or an untranslated RNA. The expression cassette containing a target polynucleotide sequence may be chimeric, it means that at least one of components thereof is heterologous to at least one of the other components. The expression cassette may also be naturally existent, but obtained by efficient recombination for heterologous expression.

According to a typical embodiment of the present disclosure, a recombinant plasmid is provided. The recombinant plasmid contains any one of the above DNA molecules. The DNA molecule in the above recombinant plasmid is in an appropriate position of the recombinant plasmid, so that the DNA molecule may be replicated, transcriped or expressed correctly and smoothly.

Although a qualifier used in the present disclosure to define the above DNA molecule is "containing", it does not mean that other sequences that are not related to functions thereof may be arbitrarily added to both ends of the DNA sequence. Those skilled in the art know that in order to meet the requirements of a recombination operation, it is necessary to add suitable restriction endonuclease cleavage sites at both ends of the DNA sequence, or to additionally add a start codon, a stop codon and the like, therefore, if the closed expression is used to define, these situations may not be truly covered.

A term "plasmid" used in the present disclosure includes any plasmids, cosmids, bacteriophages or *Agrobacterium* binary nucleic acid molecules in double-stranded or single-stranded linear or circular form, preferably a recombinant expression plasmid, it may be a prokaryotic expression plasmid, or a eukaryotic expression plasmid, but preferably the prokaryotic expression plasmid. In some embodiments, the recombinant plasmid is selected from pET-22a(+), pET-22b(+), pET-3a(+), pET-3d(+), pET-11a(+), pET-12a(+), pET-14b(+), pET-15b(+), pET-16b(+), pET-17b(+), pET-19b (+), pET-20b(+), pET-21a(+), pET-23a(+), pET-23b(+), pET-24a(+), pET-25b(+), pET-26b(+), pET-27b(+), pET-28a (+), pET-29a(+), pET-30a(+), pET-31 b(+), pET-32a(+), pET-35b(+), pET-38b(+), pET-39b(+), pET-40b(+), pET-41a (+), pET-41 b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b(+).

According to a typical embodiment of the present disclosure, a host cell is provided. The host cell contains any one of the above recombinant plasmids. The host cell suitable for the present disclosure includes but is not limited to a prokaryotic cell, yeast or a eukaryotic cell. Preferably, the prokaryotic cell is eubacteria, for example gram-negative bacteria or gram-positive bacteria. More preferably, the prokaryotic cell is an *E. coli* BL21 cell or an *E. coli* DH5α competent cell.

According to a typical embodiment of the present disclosure, a method for producing a chiral amine is provided. The method includes a step of catalyzing a transamination reaction of a ketone compound and an amino donor by a transaminase, and the transaminase is any one of the above transaminase mutants. Because the above transaminase mutant of the present disclosure acquires the catalytic activity on the carbonyl substrate, and the catalytic effect is better. Some of the mutants also acquire the catalytic activity on the sitagliptin precursor ketone, and improve the stability and tolerance of the enzyme, the amount of the enzyme used is reduced, and the difficulty of post-treatment is reduced.

Further, the ketone compound is

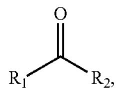

and a product of the transamination reaction is

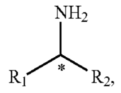

herein, $R_1$ and $R_2$ each independently represent an optionally substituted or unsubstituted alkyl, an optionally substituted or unsubstituted aralkyl, or an optionally substituted or unsubstituted aryl; and the $R_1$ and $R_2$ may be singly or combined with each other to form a substituted or unsubstituted ring.

Preferably, the $R_1$ and $R_2$ are an optionally substituted or unsubstituted alkyl having 1 to 20 carbon atoms, an optionally substituted or unsubstituted aralkyl, or an optionally substituted or unsubstituted aryl, more preferably an optionally substituted or unsubstituted alkyl having 1 to 10 carbon atoms, an optionally substituted or unsubstituted aralkyl, or an optionally substituted or unsubstituted aryl.

Preferably, the aryl includes a phenyl, a naphthyl, a pyridyl, a thienyl, an oxadiazolyl, an imidazolyl, a thiazolyl, a furyl, a pyrrolyl, a phenoxy, a naphthyloxy, a pyridyloxy, a thienyloxy, an oxadiazolyloxy, an imidazolyloxy, a thiazolyloxy, a furyloxy or a pyrrolyloxy.

Preferably, the alkyl includes a methyl, an ethyl, a propyl, a butyl, a pentyl, a hexyl, an isopropyl, a sec-butyl, a tert-butyl, a methoxy, an ethoxy, a tert-butoxy, a methoxycarbonyl, an ethoxycarbonyl, a tert-butoxycarbonyl, a vinyl, an allyl, a cyclopentyl or a cycloheptyl.

Preferably, the aralkyl is a benzyl.

Preferably, the substitution refers to substitution by a halogen atom, a nitrogen atom, a sulfur atom, a hydroxyl, a nitro group, a cyano group, a methoxy, an ethoxy, a carboxyl, a carboxymethyl, a carboxyethyl or a methylenedioxy.

Preferably, the ketone compound is

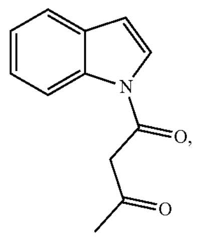

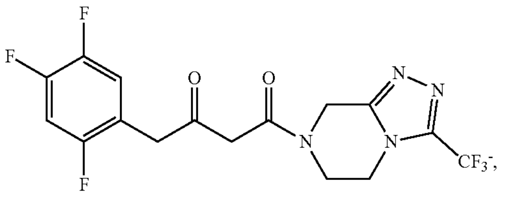

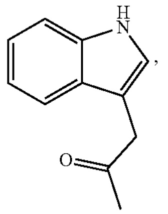

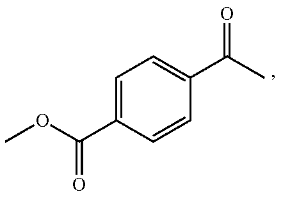

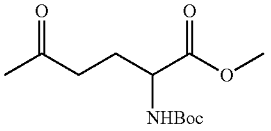

or

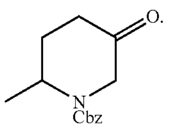

In a typical embodiment of the present disclosure, the amino donor is isopropylamine or alanine, preferably isopropylamine.

In a reaction system in which the transaminase of the present disclosure is applied to catalyze the transamination reaction of the ketone compound and the amino donor, a pH is 7-11, preferably 8-10, and more preferably 9-10, it means that the value of the pH may be a value optionally selected from 7-11, for example 7, 7.5, 8, 8, 8.6, 9, 10, 10.5 and the like. The temperature of the reaction system in which the transaminase catalyzes the transamination reaction of the ketone compound and the amino donor is 25-60° C., more preferably 30-55° C., further preferably 40-50° C., in other words, the value of the temperature may be a value optionally selected from 25-60° C., for example 30, 31, 32, 35, 37, 38, 39, 40, 42, 45, 48, 50, 51, 52, 55 and the like. The volume concentration of dimethyl sulfoxide in the reaction system in which the transaminase catalyzes the transamination reaction of the ketone compound and amino donor is 0%-50%, for example 10%, 15%, 18%, 20%, 30%, 35%, 38%, 40%, 42%, 48%, 49% and the like. The volume concentration of methyl tert-butyl ether in the reaction system in which the transaminase catalyzes the transamination reaction of the ketone compound and amino donor is 0%-90%, for example, 10%, 16%, 18%, 20%, 30%, 35%, 38%, 40%, 42%, 48%, 49%, 55%, 60%, 70%, 80%, 90% and the like.

Those skilled in the art know that many modifications may be made to the present disclosure without departing from the spirit of the present disclosure, and such modifications also fall within a scope of the present disclosure. In addition, the following experimental methods are conventional methods unless otherwise specified, and experimental materials used may be easily obtained from commercial companies unless otherwise specified.

Embodiment 1

Catalytic activity of SsTA wild enzyme and mutant thereof on sitagliptin precursor ketone

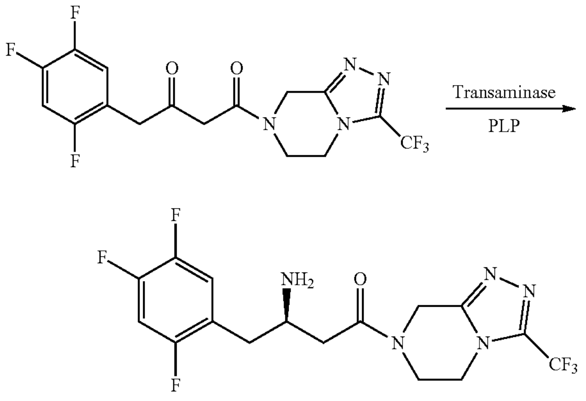

In a 100 mL reaction flask, 100 mg a raw material is weighed, 1 mg 5'-pyridoxal phosphate is added, 3.7 mM isopropylamine hydrochloride is added, 1.5 mL crude enzyme solution of SsTA mutant or wild enzyme (0.2 g mutant wet cells are broken by ultrasonic to prepare 20% crude enzyme solution, pH=8.0) is added, and 100 mM PB8.0 is added so that a final volume of a system is 5 mL, it is stirred at 45° C. of a constant temperature for 16 h, the system is centrifuged at 12000 rpm for 5 min, 200 μL a sample is taken, and 2 mL acetonitrile is added to dissolve, after being centrifuged at 12000 rpm for 5 min, it is sent to a High Performance Liquid Chromatograph (HPLC) to detect a conversion rate and an enantiomeric excess (ee) value of a product. It may be seen from the results in Table 4 that SsTA wild bacteria have no catalytic activity on the substrate, while the SsTA mutant may generate more than 90% of chiral amine products, and the chiral purity is >98% by ee value detection. After the modification of the present disclosure, the SsTA mutant acquires the catalytic activity on the substrate sitagliptin precursor ketone with the larger steric hindrance, and the activity of some mutants is greatly improved, so the substrate spectrum is expanded.

TABLE 4

| Strain | Amino acid difference (compared to SsTA) | Activity |
|---|---|---|
| SsTA | No | ND |
| M57 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + S207I + V244M + K211H + F208R + T290S + A292G | 90.74% |
| M58 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R | 98.61% |
| M59 | MTTTEFANREIH + G17V + Q40H + T66M + G69Y + H70T + L73A + V77G + A78I + K141S + K142T + R143P + G144Y + K146R + E145G + Y130M + L148A + L151H + T152R + H153P + I160F + L163Q + A165I + R188L + T204N + S207I + K211H + F208R + T290S + A292G | 91.43% |
| M88 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + R273T | 96.51% |
| M89 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + D327M | 93.34% |
| M90 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + V244H | 95.47% |
| M91 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211Q + F208R + S207I + T290S + A292G + S278R + R273T | 93.27% |

Embodiment 2

Generation of chiral amine from ketone compound catalyzed by SsTA wild enzyme and mutant thereof

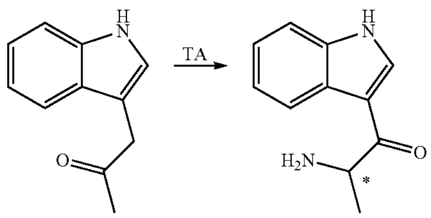

In a 100 mL reaction flask, 100 mg a raw material is weighed, 1 mg 5'-pyridoxal phosphate is added, 3.7 mM isopropylamine hydrochloride is added, 5 mL crude enzyme solution of SsTA mutant or wild enzyme (1 g mutant wet cells are broken by ultrasonic to prepare 20% crude enzyme solution, pH=8.0) is added, and 100 mM PB8.0 is added so that a final volume of a system is 7 mL, it is stirred at 30° C. of a constant temperature for 16 h, the system is centrifuged at 12000 rpm for 5 min, 200 μL a sample is taken, and 2 mL acetonitrile is added to dissolve, after being centrifuged at 12000 rpm for 5 min, it is sent to a HPLC to detect a conversion rate and an ee value of a product. It may be seen from the results in Table 5 that SsTA wild bacteria have no catalytic activity on the substrate, while the SsTA mutant may generate more than 40% of chiral amine products, and the chiral purity is >98% by ee value detection. After the modification of the present disclosure, the catalytic substrate spectrum of the SsTA mutant is expanded.

TABLE 5

| Strain | Amino acid difference (compared to SsTA) | Activity |
|---|---|---|
| SsTA | No | ND |
| M38 | MTTTEFANREFH + G69Y + H70T + L73A + V77G + A78I + K141S + K142T + R143P + G144Y + L148A + L151A + T152R + A165I + Y130V + L163Q + K211H + F208R + R188L + S207I + T290S + A292G | ++ |
| M39 | MTTTEFANREIH + G69Y + H70T + L73A + V77G + A78I + K141S + K142T + R143P + G144Y + L148A + L151A + T152R + R188L + A165I + L163Q + Y130V + K211H + F208R + S207I + T290S + A292G + G17V + Q40H + T204S | ++ |
| M40 | MTTTEFANREFH + G69Y + H70T + L73A + V77G + A78I + K141S + K142T + R143P + G144Y + L148A + L151A + T152R + R188L + A165I + Y130V + L163Q + K211H + F208R + S207I + T290S + A292G + T204S | +++ |
| M41 | MTTTEFANREIH + G17V + Q40H + T66M + G69Y + H70T + L73A + V77G + A78I + K141S + K142T + R143P + G144Y + A165I + Y130V + L163Q + L148A + L151A + T152R + R188L + T204S + S207I + K211H + F208R + T290S + A292G | +++ |
| M42 | MTTTEFANREIH + G17V + Q40H + T66M + G69Y + H70T + L73A + V77G + A78I + K141S + K142T + R143P + G144Y + E145S + Y130V + L148A + L151A + T152R + L163Q + A165I + R188L + T204S + S207I + F208R + K211H + T290S + A292G | +++ |

TABLE 5-continued

| Strain | Amino acid difference (compared to SsTA) | Activity |
|---|---|---|
| M43 | MTTTEFANREFH + G17V + Q40H + T66M + G69Y + H70T + L73A + V77G + A78I + K141T + K142S + R143P + G144Y + K146R + E145G + Y130V + L148A + L151H + T152R + H153P + L163Q + A165I + R188L + T204S + S207I + F208R + K211H + T290S + A292G | ++ |
| M44 | MTTTEFANREIH + G17V + Q40H + T66M + G69Y + H70T + L73A + V77G + A78I + K141S + K142T + R143P + G144Y + A165I + Y130M + 163Q + L148A + L151E + T152R + R188L + T204S + K211H + F208R + S207I + T290S + A292G | ++ |
| M45 | MTTTEFANREIH + G17V + Q40H + T204S + T66M + G69Y + H70T + L73A + V77G + A78I + K141S + K142T + R143P + G144Y + Y130V + L148A + L151H + T152R + H153P + L163Q + A165I + R188L + K211H + F208R + S207I + T290S + A292G | +++ |
| M46 | MTTTEFANREFH + G17V + Q40H + T66M + G69Y + H70T + L73A + V77G + A78I + Y130M + K141S + K142T + R143P + G144Y + L148A + L151H + T152R + H153P + L163Q + A165I + R188L + T204S + K211H + F208R + S207I + T290S + A292G | +++ |
| M47 | MTTTEFANREIH + G17V + Q40H + T66M + G69Y + H70T + L73A + V77G + A78I + K141S + K142T + R143P + G144Y + Y130V + L148A + L151E + T152R + L163Q + A165I + R188L + T204S + S207I + F208R + K211H + T290S + A292G | +++ |
| M48 | MTTTEFANREFH + G17V + Q40H + T66M + G69Y + H70T + L73A + V77G + A78I + K141S + K142T + R143P + G144Y + Y130V + L148A + L151H + T152R + H153P + L163Q + A165I + R188L + Y198F + T204S + F208R + S207I + K211H + T290S + A292G | +++ |
| M50 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + T204S + K211H + F208R + S207I + T290S + A292G | +++ |
| M51 | MTTTEFANREFH + T66A + G69Y + H70T + L73A + V77G + A78I + K141S + K142T + R143P + G144Y + Y130V + L148A + L151A + T152R + L163Q + A165I + G187S + K211H + F208R + S207I + T290S + A292G | +++ |
| M52 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + K211H + F208R + T204S + S207I + T290S + A292G | +++ |
| M55 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G | ++++ |
| M56 | MTTTEFANREIH + G17V + Q40H + T66M + G69Y + H70T + L73A + V77G + A78I + K141S + K142T + R143P + G144Y + Y130M + K146R + E145G + L148A + L151V + H153P + T152R + A165I + L163Q + R188L + T204S + S207I + K211H + F208R + T290S + A292G | ++++ |
| M57 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + S207I + V244M + K211H + F208R + T290S + A292G | ++++ |
| M58 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R | ++++ |

ND means that no product is detected,
+ means that 1%-10% of the product generation is detected,
++ means that 10%-20% of the product generation is detected,
+++ means that 20%-30% of the product generation is detected,
and ++++ means that 40%-50% of the product generation is detected.

Embodiment 3

Generation of chiral amine from ketone compound catalyzed by SsTA wild enzyme and mutant thereof

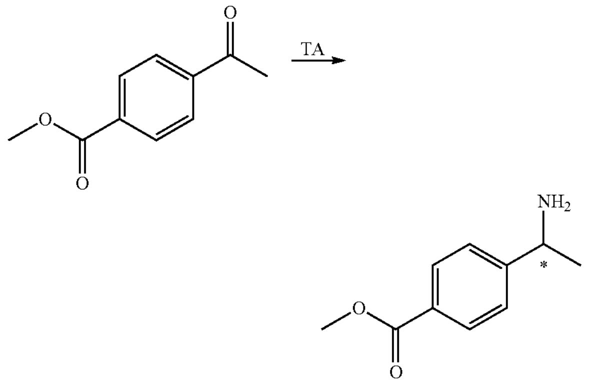

In a 100 mL reaction flask, 100 mg a raw material is weighed, 1 mg 5'-pyridoxal phosphate is added, 3.7 mM isopropylamine hydrochloride is added, 5 mL crude enzyme solution of SsTA mutant or wild enzyme (1 g mutant wet cells are broken by ultrasonic to prepare 20% crude enzyme solution, pH=8.0) is added, and 100 mM PB8.0 is added so that a final volume of a system is 7 mL, it is stirred at 30° C. of a constant temperature for 16 h, the system is centrifuged at 12000 rpm for 5 min, 200 μL a sample is taken, and 2 mL acetonitrile is added to dissolve, after being centrifuged at 12000 rpm for 5 min, it is sent to a HPLC to detect a conversion rate and an ee value of a product. It may be seen from the results in Table 6 that SsTA wild bacteria have no catalytic activity on the substrate, while the SsTA mutant may generate more than 40% of chiral amine products. After the modification of the present disclosure, the catalytic substrate spectrum of the SsTA mutant is expanded.

TABLE 6

| Strain | Amino acid difference (compared to SsTA) | Activity |
|---|---|---|
| SsTA | No | ND |
| M44 | MTTTEFANREIH + G17V + Q40H + T66M + G69Y + H70T + L73A + V77G + A78I + K141S + K142T + R143P + G144Y + A165I + Y130M + 163Q + L148A + L151E + T152R + R188L + T204S + K211H + F208R + S207I + T290S + A292G | +++ |
| M45 | MTTTEFANREIH + G17V + Q40H + T204S + T66M + G69Y + H70T + L73A + V77G + A78I + K141S + K142T + R143P + G144Y + Y130V + L148A + L151H + T152R + H153P + L163Q + A165I + R188L + K211H + F208R + S207I + T290S + A292G | +++ |
| M55 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G | ++++ |
| M57 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + S207I + V244M + K211H + F208R + T290S + A292G | ++++ |
| M58 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R | ++++ |

ND means that no product is detected,
+++ means that 30%-40% of the product generation is detected,
and ++++ means that 40%-50% of the product generation is detected.

Embodiment 4

Generation of chiral amine from ketone compound catalyzed by SsTA wild enzyme and mutant thereof

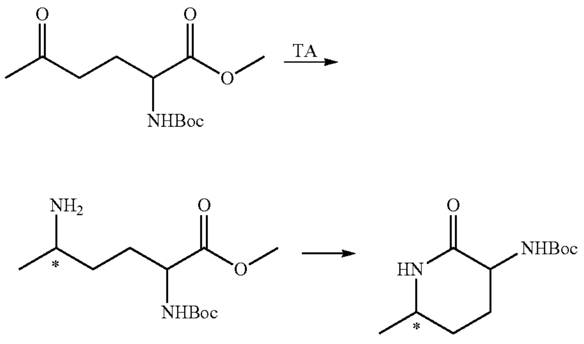

In a 100 mL reaction flask, 100 mg a raw material is weighed, 1 mg 5'-pyridoxal phosphate is added, 3.7 mM isopropylamine hydrochloride is added, 5 mL crude enzyme solution of SsTA mutant or wild enzyme (1 g mutant wet cells are broken by ultrasonic to prepare 20% crude enzyme solution, pH=8.0) is added, and 100 mM PB8.0 is added so that a final volume of a system is 7 mL, it is stirred at 30° C. of a constant temperature for 16 h, the system is centrifuged at 12000 rpm for 5 min, 200 μL a sample is taken, and 2 mL acetonitrile is added to dissolve, after being centrifuged at 12000 rpm for 5 min, it is sent to a HPLC to detect a conversion rate and an ee value of a product. It may be seen from the results in Table 7 that SsTA wild bacteria have no catalytic activity on the substrate, while the SsTA mutant may generate more than 40% of chiral amine products. After the modification of the present disclosure, the catalytic substrate spectrum of the SsTA mutant is expanded.

TABLE 7

| Strain | Amino acid difference (compared to SsTA) | Activity |
|---|---|---|
| SsTA | No | ND |
| M16 | G69Y + H70T + L73A + V77G + A781 + K141S + K142S + R143P + G144F + S207I + T290S + A292G + A165I + F144W + Y198F | +++ |
| M26 | G69Y + H70T + L73A + V77G + A78I + K141S + K142S + R143P + G144F + A165I + Y130M + L163Q + L151A + S207I + F208R + K211H + T290S + A292G | +++ |
| M35 | MTTTEFANREFH + G69Y + H70T + L73A + V77G + A78I + K141S + K142T + R143P + G144Y + L148A + L151A + T152R + A165I + Y130M + L163Q + K211H + F208R + S207I + T290S + A292G | +++ |
| M50 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + T204S + K211H + F208R + S207I + T290S + A292G | ++++ |

ND means that no product is detected,
+++ means that 30%-40% of the product generation is detected,
and ++++ means that 40%-50% of the product generation is detected.

Embodiment 5

Generation of chiral amine from ketone compound catalyzed by SsTA wild enzyme and mutant thereof

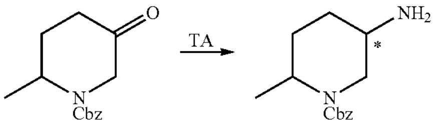

In a 100 mL reaction flask, 100 mg a raw material is weighed, 1 mg 5'-pyridoxal phosphate is added, 3.7 mM isopropylamine hydrochloride is added, 5 mL crude enzyme solution of SsTA mutant or wild enzyme (1 g mutant wet cells are broken by ultrasonic to prepare 20% crude enzyme solution, pH=8.0) is added, and 100 mM PB8.0 is added so that a final volume of a system is 7 mL, it is stirred at 30° C. of a constant temperature for 16 h, the system is centrifuged at 12000 rpm for 5 min, 200 μL a sample is taken, and 2 mL acetonitrile is added to dissolve, after being centrifuged at 12000 rpm for 5 min, it is sent to a HPLC to detect a conversion rate and an ee value of a product. It may be seen from the results in Table 8 that SsTA wild bacteria have no catalytic activity on the substrate, while the SsTA mutant may generate more than 90% of chiral amine products, and the shiral purity is very high and is 99%. After the modification of the present disclosure, the catalytic substrate spectrum of the SsTA mutant is expanded.

TABLE 8

| Strain | Amino acid difference (compared to SsTA) | Activity |
|---|---|---|
| SsTA | No | ND |
| M6 | G69Y + H70T + L73A + V77G + A78I + K141S + K142S + R143P + G144F + S207I + T290S + A292G + A165I | ++ |
| M7 | G69Y + H70T + L73A + V77G + A78I + K141S + K142S + R143P + G144F + S207I + T290S + A292G + A165I + Y198M + F144W | ++ |
| M9 | G69Y + H70T + L73A + V77G + A78I + K141S + K142S + R143P + G144F + S207I + T290S + A292G + A165I + R216Q | ++++ |
| M10 | G69Y + H70T + L73A + V77G + A78I + K141S + K142S + R143P + G144F + S207I + T290S + A292G + A165I + R216S | +++ |
| M11 | G69Y + H70T + L73A + V77G + A78I + K141S + K142S + R143P + G144F + S207I + T290S + A292G + A165I + Y198F | ++ |
| M12 | G69Y + H70T + L73A + V77G + A78I + K141S + K142S + R143P + G144F + S207I + T290S + A292G + A165I + F208R | +++ |
| M13 | G69Y + H70T + L73A + V77G + A78I + K141S + K142S + R143P + G144F + S207I + T290S + A292G + A165I + T204N | +++ |
| M15 | G69Y + H70T + L73A + V77G + A78I + K141S + K142S + R143P + G144F + S207I + T290S + A292G + A165I + F144W + Y198F | ++ |
| M23 | G69Y + H70T + L73A + V77G + A78I + K141S + K142T + R143P + G144F + A165I + Y130M + L163Q + K211H + F208R + S207I + T290S + A292G | + |
| M30 | MTTTEFANREFH + G69Y + H70T + L73A + V77G + A78I + K141S + K142T + R143P + G144Y + L148A + L151A + A165I + Y130M + L163Q + K211H + F208R + S207I + T290S + A292G | + |
| M38 | MTTTEFANREFH + G69Y + H70T + L73A + V77G + A78I + K141S + K142T + R143P + G144Y + L148A + L151A + T152R + A165I + Y130V + L163Q + K211H + F208R + R188L + S207I + T290S + A292G | + |
| M42 | MTTTEFANREIH + G17V + Q40H + T66M + G69Y + H70T + L73A + V77G + A78I + K141S + K142T + R143P + G144Y + E145S + Y130V + L148A + L151A + T152R + L163Q + A165I + R188L + T204S + S207I + F208R + K211H + T290S + A292G | ++ |
| M43 | MTTTEFANREFH + G17V + Q40H + T66M + G69Y + H70T + L73A + V77G + A78I + K141T + K142S + R143P + G144Y + K146R + E145G + Y130V + L148A + L151H + T152R + H153P + L163Q + A165I + R188L + T204S + S207I + F208R + K211H + T290S + A292G | ++++ |
| M44 | MTTTEFANREIH + G17V + Q40H + T66M + G69Y + H70T + L73A + V77G + A78I + K141S + K142T + R143P + G144Y + A165I + Y130M + 163Q + L148A + L151E + T152R + R188L + T204S + K211H + F208R + S207I + T290S + A292G | ++++ |
| M48 | MTTTEFANREFH + G17V + Q40H + T66M + G69Y + H70T + L73A + V77G + A78I + K141S + K142T + R143P + G144Y + Y130V + L148A + L151H + T152R + H153P + L163Q + A165I + R188L + Y198F + T204S + F208R + S207I + K211H + T290S + A292G | +++ |
| M52 | MTTTEFANREIH + G17V + Q40H + T66Q + G69Y + H70T + L73A + V77G + A78I + K141S + K142T + R143P + G144Y + Y130V + L148A + L151A + T152R + L163Q + A165I + R188L + K211H + F208R + T204S + S207I + T290S + A292G | ++ |
| M58 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R | ++++ |
| M88 | MTTTEFANREIH + G17V + Q40H + T66M + G69Y + H70T + L73A + V77G + A78I + K141S + K142T + R143P + G144Y + Y130M + K146R + E145G + L148A + L151H + T152R + H153P + L163Q + A165I + R188L + T204N + K211H + F208R + S207I + T290S + A292G + S278R + R273T | ++++ |

ND means that no product is detected,

+++ means that 30%-40% of the product generation is detected, and ++++ means that 40%-50% of the product generation is detected.

It may be seen from the above descriptions that the above embodiments of the present disclosure achieve the following technical effects: the SsTA wild type in the existing technology have no catalytic activity on the substrate, and the modified mutant has the expanded substrate spectrum. At the same time, the stability of the enzyme is improved, so that the optimal reaction temperature thereof is significantly increased, and the solvent tolerance is improved, it may be applied to the stringent reaction conditions.

The above are only preferred embodiments of the present disclosure, and are not used to limit the present disclosure. For those skilled in the art, the present disclosure may have various modifications and changes. Any modifications, equivalent replacements, improvement and the like made within the spirit and principle of the present disclosure should be included in a scope of protection of the present disclosure.

The invention claimed is:

1. A transaminase mutant comprising an amino acid sequence having 80% identity with SEQ ID NO: 1 and mutations H70T+V77G.

2. The transaminase mutant of claim 1, wherein the mutation at least comprises at least one of the following mutation site combinations: H70T+L73A+V77G+A78I+K141S+R143P+S207I+T290S+A292G and H70T+L73A+V77G+G144F/Y/W+S207I.

3. The transaminase mutant of claim 2, wherein the mutation at least comprises at least one of the following mutation site combinations: G69Y+H70T+L73A+V77G+A78I+K141S+K142S+R143P+G144F+S207I+T290S+A292G, G69Y+H70T+L73A+V77G+A78I+K141S+K142S+R143P+G144F+S207I+T290S+A292G+A165I, G69Y+H70T+L73A+V77G+A78I+K141S+K142S+R143P+G144W+S207I+T290S+A292G+A165I+Y198M, G69Y+H70T+L73A+V77G+A78I+K141S+K142S+R143P+G144F+S207I+T290S+A292G+A165I+Y198M, G69Y+H70T+L73A+V77G+A78I+K141S+K142S+R143P+G144F+S207I+T290S+A292G+A165I+R216Q, G69Y+H70T+L73A+V77G+A78I+K141S+K142S+R143P+G144F+S207I+T290S+A292G+A165I+R216S, G69Y+H70T+L73A+V77G+A78I+K141S+K142S+R143P+G144F+S207I+T290S+A292G+A165I+Y198F, G69Y+H70T+L73A+V77G+A78I+K141S+K142S+R143P+G144F+S207I+T290S+A292G+A165I+F208R, G69Y+H70T+L73A+V77G+A78I+K141S+K142S+R143P+G144F+S207I+T290S+A292G+A165I+T204N, G69Y+H70T+L73A+V77G+A78I+K141S+K142S+R143P+G144F+S207I+T290S+A292G+A165I+K211H, G69Y+H70T+L73A+V77G+A78I+K141S+K142S+R143P+G144F+S207I+T290S+A292G+A165I+F144W+Y198F, G69Y+H70T+L73A+V77G+A78I+K141S+K142S+R143P+G144W+S207I+T290S+A292G+A165I+Y198F+K211H, G69Y+H70T+L73A+V77G+A78I+K141S+K142S+R143P+G144F+S207I+A165I+Y130M+163Q+T290S+A292G, G69Y+H70T+L73A+V77G+A78I+K141S+K142S+R143P+G144F+A165I+Y130M+L163Q+Y198F+S207I+T290S+A292G, G69Y+H70T+L73A+V77G+A78I+K141S+K142S+R143P+G144F+A165I+Y130M+L163Q+Y158S+I160C+N132T+S207I+T290S+A292G, G69Y+H70T+L73A+V77G+A78I+K141S+K142S+R143P+G144F+A165I+Y130M+L163Q+K211H+F208R+S207I+T290S+A292G, G69Y+H70T+L73A+V77G+A78I+K141S+K142S+R143P+G144F+A165I+Y130M+L163Q+Y158S+I160C+S207I+T290S+A292G, G69Y+H70T+L73A+V77G+A78I+K141S+K142T+R143P+G144F+A165I+Y130M+L163Q+K211H+F208R+S207I+T290S+A292G, G69Y+H70T+L73A+V77G+A78I+K141S+K142S+R143P+G144F+L148A+A165I+Y130M+L163Q+K211H+F208R+S207I+T290S+A292G, G69Y+H70T+L73A+V77G+A78I+K141S+K142S+R143P+G144F+L148I+A165I+Y130M+L163Q+K211H+F208R+S207I+T290S+A292G, G69Y+H70T+L73A+V77G+A78I+K141S+K142S+R143P+G144F+A165I+Y130M+L163Q+L151A+S207I+F208R+K211H+T290S+A292G, G69Y+H70T+L73A+V77G+A78I+K141S+K142S+R143P+G144F+P180A+A165I+Y130M+L163Q+F208R+S207I+K211H+T290S+A292G, G69Y+H70T+L73A+V77G+A78I+K141S+K142T+R143P+G144F+L148A+L151A+A165I+Y130M+L163Q+K211H+F208R+S207I+T290S+A292G, G69Y+H70T+L73A+V77G+A78I+K141S+K142T+R143P+G144F+L148A+L151A+A165I+Y130M+L163R+K211H+F208R+S207I+T290S+A292G, MTTTEFANREFH+G69Y+H70T+L73A+V77G+A78I+K141S+K142T+R143P+G144Y+L148A+L151A+A165I+Y130M+L163Q+K211H+F208R+S207I+T290S+A292G, G69Y+H70T+L73A+V77G+A78I+Y130V+K141S+K142T+R143P+G144F+E145D+L148T+L151A+A165I+LL163Q+F208R+S207I+K211H+T290S+A292G, MTTTEFANREFH+G69Y+H70T+L73A+V77G+A78I+K141S+K142T+R143P+G144Y+L148A+L151A+Y130T+L163Q+A165I+K211H+F208R+S207I+T290S+A292G, MTTTEFANREFH+G69Y+H70T+L73A+V77G+A78I+K141S+K142T+R143P+G144Y+L148A+L151A+A165I+Y130V+L163Q+K211H+F208R+S207I+T290S+A292G, MTTTEFANREFH+G69Y+H70T+L73A+V77G+A78I+K141S+K142T+R143P+G144Y+L148A+L151A+A165I+Y130M+L163R+K211H+F208R+S207I+T290S+A292G, MTTTEFANREFH+G69Y+H70T+L73A+V77G+A78I+K141S+K142T+R143P+G144Y+L148A+L151A+T152R+A165I+Y130M+L163Q+K211H+F208R+S207I+T290S+A292G, MTTTEFANREFH+G69Y+H70T+L73A+V77G+A78I+K141S+K142T+R143P+G144Y+S207I+T290S+A292G+A165I+Y130M+L163Q+K211H+F208R+L148A+L151A+T152R+M130V, MTTTEFANREFH+G69Y+H70T+L73A+V77G+A78I+K141T+K142S+R143P+G144Y+L148A+L151A+P167S+A165I+Y130M+L163Q+K211H+F208R+S207I+T290S+A292G, MTTTEFANREFH+G69Y+H70T+L73A+V77G+A78I+K141S+K142T+R143P+G144Y+L148A+L151A+T152R+A165I+Y130V+L163Q+K211H+F208R+R188L+S207I+T290S+A292G, MTTTEFANREIH+G69Y+H70T+L73A+V77G+A78I+K141S+K142T+R143P+G144Y+L148A+L151A+T152R+R188L+A165I+L163Q+Y130V+K211H+F208R+S207I+T290S+A292G+G17V+Q40H+T204S, MTTTEFANREFH+G69Y+H70T+L73A+V77G+A78I+K141S+K142T+R143P+G144Y+L148A+L151A+T152R+R188L+A165I+Y130V+L163Q+K211H+F208R+S207I+T290S+A292G+T204S, MTTTEFANREIH+G17V+Q40H+T66M+G69Y+H70T+L73A+V77G+A78I+K141S+K142T+R143P+G144Y+A165I+Y130V+L163Q+L148A+L151A+T152R+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+E145S+Y130V+L148A+L151A+T152R+L163Q+A165I+R188L+T204S+S207I+F208R+K211H+T290S+A292G, MTTTEFANREFH+G17V+Q40H+T66M+G69Y+H70T+L73A+V77G+A78I+K141T+K142S+R143P+G144Y+K146R+E145G+Y130V+L148A+L151H+T152R+H153P+L163Q+A165I+R188L+T204S+S207I+F208R+K211H+T290S+A292G, MTTTEFANREIH+G17V+Q40H+T66M+G69Y+H70T+

L73A+V77G+A78I+K141S+K142T+R143P+G144Y+A165I+Y130M+163Q+L148A+L151E+T152R+R188L+T204S+K211H+F208R+S207I+T290S+A292G, MTTTEFANREIH+G17V+Q40H+T204S+T66M+G69Y+H70T+L73A+V77G+A78I+K141S+K142T+R143P+G144Y+Y130V+L148A+L151H+T152R+H153P+L163Q+A165I+R188L+K211H+F208R+S207I+T290S+A292G, MTTTEFANREFH+G17V+Q40H+T66M+G69Y+H70T+L73A+V77G+A78I+Y130M+K141S+K142T+R143P+G144Y+L148A+L151H+T152R+H153P+L163Q+A165I+R188L+T204S+K211H+F208R+S207I+T290S+A292G, MTTTEFANREIH+G17V+Q40H+T66M+G69Y+H70T+L73A+V77G+A78I+K141S+K142T+R143P+G144Y+Y130V+L148A+L151E+T152R+L163Q+A165I+R188L+T204S+S207I+F208R+K211H+T290S+A292G, MTTTEFANREFH+G17V+Q40H+T66M+G69Y+H70T+L73A+V77G+A78I+K141S+K142T+R143P+G144Y+Y130V+L148A+L151H+T152R+H153P+L163Q+A165I+R188L+Y198F+T204S+F208R+S207I+K211H+T290S+A292G, MTTTEFANREIH+G17V+Q40H+T66Q+G69Y+H70T+L73A+V77G+A78I+K141S+K142T+R143P+G144Y+Y130V+L148A+L151A+T152R+L163Q+A165I+R188L+T204S+K211H+F208R+S207I+T290S+A292G, MTTTEFANREFH+T66A+G69Y+H70T+L73A+V77G+A78I+K141S+K142T+R143P+G144Y+Y130V+L148A+L151A+T152R+L163Q+A165I+G187S+K211H+F208R+S207I+T290S+A292G, MTTTEFANREIH+G17V+Q40H+T66Q+G69Y+H70T+L73A+V77G+A78I+K141S+K142T+R143P+G144Y+Y130V+L148A+L151A+T152R+L163Q+A165I+R188L+K211H+F208R+T204S+S207I+T290S+A292G, MTTTEFANREIH+G17V+Q40H+G69Y+H70T+L73A+V77G+A78I+E105D+K141S+K142T+R143P+G144Y+Y130V+L148A+L151A+T152R+L163Q+A165I+R188L+T204S+K211H+F208R+S207I+T290S+A292G, MTTTEFANREIH+G17V+Q40H+G69Y+H70T+L73A+V77G+A78I+K141S+K142T+R143P+G144Y+E145G+A165I+Y130V+L163Q+L148A+L151A+T152R+R188L+T204S+K211H+F208R+S207I+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151V+H153P+T152R+A165I+L163Q+R188L+T204S+S207I+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+S207I+V244M+K211H+F208R+T290S+A292G, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R, MTTTEFANREIH+G17V+Q40H+T66M+G69Y+H70T+L73A+V77G+A78I+K141S+K142T+R143P+G144Y+K146R+E145G+Y130M+L148A+L151H+T152R+H153P+I160F+L163Q+A165I+R188L+T204N+S207I+K211H+F208R+T290S+A292G, MTTTEFANREIH+G17V+Q40H+T66M+G69Y+H70T+L73A+V77G+A78I+K141S+K142T+R143P+G144Y+K146R+E145G+Y130M+L148A+L151H+T152R+H153P+L163Q+A165I+R188L+T204N+K211H+F208R+S207I+T290S+A292G+V244E, MTTTEFANREIH+G17V+Q40H+T66M+G69Y+H70T+L73A+V77G+A78I+K141S+K142T+R143P+G144Y+Y130V+L148A+L151H+T152R+H153P+I160V+L163Q+A165I+R188L+T204S+S207I+K211H+F208R+T290S+A292G, G17V+Q40H+T66M+G69Y+H70T+L73A+V77G+A78I+K141S+K142T+R143P+G144Y+K146R+E145G+Y130M+L148A+L151H+T152R+H153P+L163Q+A165I+R188L+T204S+S207I+K211H+F208R+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+Y260F+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211Q+F208R+S207I+T290S+A292G+S278R, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+R273C, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+A242T+T290S+A292G+S278R+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+K150N+Y158N, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+V244M, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+Y158N, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+S278R, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+R273S, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+T3S+Y260F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211Q+T290S+A292G+K146R+E145G, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204S+S207I+F208R+K211H+T290S+A292G+K146R+E145G+I160F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+I160F+A242T, MTTTEFANREIH+G17V+Q40H+T66M+G69Y+H70T+L73A+V77G+A78I+

K141S+K142T+R143P+G144Y+Y130M+L148A+L151H+T152R+H153P+L163Q+A165I+R188L+T204N+S207I+F208R+K211H+T290S+A292G+K146R+E145G+Y162F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+V244E, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+V244A, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+Y260N+E261D+F322Y, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+Y260F, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T134A, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+S278R, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T270A+E282K, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+R273C, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+T175A+R273C, MTTTEFANREIH+G17V+Q40H+T66M+G69Y+H70T+L73A+V77G+A78I+K141S+K142T+R143P+G144Y+Y130M+L148A+L151Q+T152R+H153P+L163Q+A165I+R188L+T204N+S207I+F208R+K211H+T290S+A292G+K146R+E145G, MTTTEFANREIH+G17V+Q40H+T66M+G69Y+H70T+L73A+V77G+A78I+K141S+K142T+R143P+G144Y+Y130M+L148A+L151H+T152R+H153P+L163Q+A165I+R188L+T204N+S207I+F208R+K211H+T290S+A292G+K146R+E145G+L237Q, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+R273T, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+D327M, MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211H+F208R+S207I+T290S+A292G+S278R+V244H, and MTTTEFANREIH+G17V+Q40H+T66M+G69Y+H70T+L73A+V77G+A78I+K141S+K142T+R143P+G144Y+Y130M+K146R+E145G+L148A+L151H+T152R+H153P+L163Q+A165I+R188L+T204N+K211Q+F208R+S207I+T290S+A292G+S278R+R273T, wherein MTTTEFANREFH is an N-terminal portion or extension of the recited transaminase.

4. A DNA molecule, wherein the DNA molecule encodes the transaminase mutant of claim 1.

5. A recombinant plasmid, wherein the recombinant plasmid comprises the DNA molecule of claim 4.

6. The recombinant plasmid of claim 5, wherein the recombinant plasmid is pET-22a(+), pET-22b(+), pET-3a(+), pET-3d(+), pET-11a(+), pET-12a(+), pET-14b(+), pET-15b (+), pET-16b(+), pET-17b(+), pET-19b(+), pET-20b(+), pET-21a(+), pET-23a(+), pET-23b(+), pET-24a(+), pET-25b (+), pET-26b(+), pET-27b(+), pET-28a(+), pET-29a(+), pET-30a(+), pET-31b(+), pET-32a(+), pET-35b(+), pET-38b (+), pET-39b(+), pET-40b(+), pET-41a(+), pET-41b(+), pET-42a(+), pET-43a(+), pET-43b(+), pET-44a(+), pET-49b (+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18, or pUC-19.

7. A host cell, wherein the host cell comprises the recombinant plasmid of claim 5.

8. The host cell of claim 7, wherein the host cell comprises a prokaryotic cell or a eukaryotic cell.

9. The host cell of claim 8, wherein the prokaryotic cell is an *E. coli* BL21 (DE3) cell or an *E. coli* BL21 (DE3) cell, and the eukaryotic cell is yeast.

10. A method for producing a chiral amine comprising a step of catalyzing a transamination reaction of a ketone compound and an amino donor by a transaminase, and the transaminase is the transaminase mutant of claim 1.

11. The method of claim 10, wherein the ketone compound is

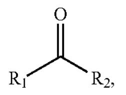

and a product of the transamination reaction is

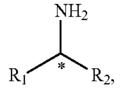

$R_1$ and $R_2$ each independently represents an substituted or unsubstituted alkyl, an substituted or unsubstituted aralkyl, or an substituted or unsubstituted aryl; and the $R_1$ and $R_2$ may be singly or combined with each other to form a substituted or unsubstituted ring.

12. The method of claim 11, wherein the $R_1$ and $R_2$ are a substituted or unsubstituted alkyl having 1 to 20 carbon atoms, a substituted or unsubstituted aralkyl, or a substituted or unsubstituted aryl.

13. The method of claim 12, wherein the aryl comprises is selected from a phenyl, a naphthyl, a pyridyl, a thienyl, an oxadiazolyl, an imidazolyl, a thiazolyl, a furyl, a pyrrolyl, a phenoxy, a naphthyloxy, a pyridyloxy, a thienyloxy, an oxadiazolyloxy, an imidazolyloxy, a thiazolyloxy, a furyloxy, and a pyrrolyloxy;

the alkyl is selected from a methyl, an ethyl, a propyl, a butyl, a pentyl, a hexyl, an isopropyl, a sec-butyl, a tert-butyl, a methoxy, an ethoxy, a tert-butoxy, a methoxycarbonyl, an ethoxycarbonyl, a tert-butoxycarbonyl, a vinyl, an allyl, a cyclopentyl, and a cycloheptyl; and the aralkyl is a benzyl.

14. The method of claim 12, wherein the a substituent for the alkyl, the aralkyl, or the aryl is selected from a halogen atom, a nitrogen atom, a sulfur atom, a hydroxyl, a nitro group, a cyano group, a methoxy, an ethoxy, a carboxyl, a carboxymethyl, a carboxyethyl, and a methylenedioxy.

15. The method of claim 12, wherein each of the $R_1$ and $R_2$ is a substituted or unsubstituted alkyl having 1 to 10 carbon atoms, an substituted or unsubstituted aralkyl, or an substituted or unsubstituted aryl.

16. The method of claim 11, wherein the ketone compound is

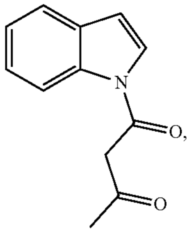

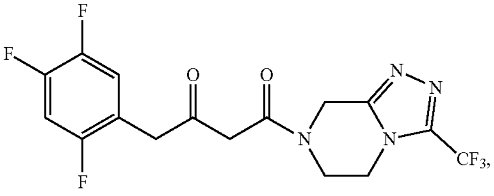

-continued

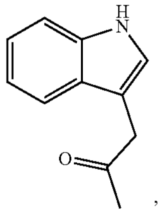
,
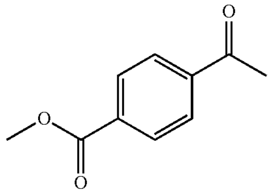
,

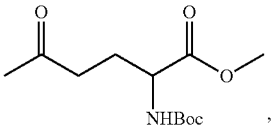
, or
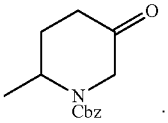
.

17. The method of claim 10, wherein the amino donor is isopropylamine or alanine.

18. The method of claim 10, wherein in a reaction system in which the transaminase catalyzes the transamination reaction of the ketone compound and the amino donor has a pH of 7-11 at a temperature of 25° C.-60° C.

19. The method of claim 18, wherein the reaction system in which the transaminase catalyzes the transamination reaction of the ketone compound and the amino donor has a pH of 8-10 and a temperature of the reaction system of 30-55° C.

20. The method of claim 19, wherein the reaction system in which the transaminase catalyzes the transamination reaction of the ketone compound and the amino donor has a pH of 9-10 temperature of the reaction system of 40-50° C.

* * * * *

SEQUENCE LISTING

```
<160> NUMBER OF SEQ ID NOS: 1

<210> SEQ ID NO 1
<211> LENGTH: 338
<212> TYPE: PRT
<213> ORGANISM: Sciscionella sp.

<400> SEQUENCE: 1

Met Thr Thr Thr Glu Phe Ala Asn Ser Asn Leu Val Ala Val Glu Pro
1               5                   10                  15

Gly Ala Ile Arg Glu Pro Thr Pro Pro Gly Ser Val Ile Gln Tyr Ser
            20                  25                  30

Glu Tyr Glu Leu Asp Arg Ser Gln Pro Leu Ala Gly Gly Val Ala Trp
        35                  40                  45

Ile Glu Gly Glu Tyr Val Pro Ala Asp Glu Ala Arg Ile Ser Ile Phe
    50                  55                  60

Asp Thr Gly Phe Gly His Ser Asp Leu Thr Tyr Thr Val Ala His Val
65                  70                  75                  80

Trp His Gly Asn Ile Phe Arg Leu Glu Asp His Leu Asp Arg Leu Leu
                85                  90                  95

His Gly Ala Ala Arg Leu Lys Leu Glu Thr Gly Met Ser Arg Glu Glu
            100                 105                 110

Leu Ala Gly Ile Ala Lys Arg Cys Val Ser Leu Ser Gln Leu Arg Glu
        115                 120                 125

Ala Tyr Val Asn Ile Thr Ile Thr Arg Gly Tyr Gly Lys Lys Arg Gly
    130                 135                 140

Glu Lys Asp Leu Thr Lys Leu Thr His Gln Val Tyr Val Tyr Ala Ile
145                 150                 155                 160

Pro Tyr Leu Trp Ala Phe Pro Pro Glu Glu Gln Ile Phe Gly Thr Ser
                165                 170                 175

Val Ile Val Pro Arg His Val Arg Arg Ala Gly Arg Asn Thr Ile Asp
            180                 185                 190

Pro Thr Ile Lys Asn Tyr Gln Trp Gly Asp Leu Thr Ala Ala Ser Phe
        195                 200                 205

Glu Ala Lys Asp Arg Gly Ala Arg Ser Ala Val Leu Leu Asp Ala Asp
    210                 215                 220

Asn Cys Val Ala Glu Gly Pro Gly Phe Asn Val Val Leu Val Lys Asp
225                 230                 235                 240

Gly Ala Leu Val Ser Pro Ser Arg Asn Ala Leu Pro Gly Ile Thr Arg
                245                 250                 255

Lys Thr Val Tyr Glu Ile Ala Ala Ala Lys Gly Ile Glu Thr Met Leu
            260                 265                 270

Arg Asp Val Thr Ser Ser Glu Leu Tyr Glu Ala Asp Glu Leu Met Ala
        275                 280                 285

Val Thr Thr Ala Gly Gly Val Thr Pro Ile Thr Ser Leu Asp Gly Glu
    290                 295                 300
```

-continued

```
Gln Val Gly Asn Gly Glu Pro Gly Pro Ile Thr Val Ala Ile Arg Asp
305                 310                 315                 320

Arg Phe Trp Ala Leu Met Asp Glu Pro Ser Ser Leu Ile Glu Ala Ile
                325                 330                 335

Asp Tyr
```